(12) United States Patent
Carter

(10) Patent No.: US 7,606,783 B1
(45) Date of Patent: Oct. 20, 2009

(54) HEALTH, SAFETY AND SECURITY ANALYSIS AT A CLIENT LOCATION

(75) Inventor: Robert M. Carter, 2791 Dover Rd. NW., Atlanta, GA (US) 30327

(73) Assignee: Robert M. Carter, Atlanta, GA (US)

( * ) Notice: Subject to any disclaimer, the term of this patent is extended or adjusted under 35 U.S.C. 154(b) by 236 days.

(21) Appl. No.: 11/382,702

(22) Filed: May 10, 2006

Related U.S. Application Data

(60) Provisional application No. 60/679,602, filed on May 10, 2005.

(51) Int. Cl.
*G06F 17/00* (2006.01)
*G06N 5/02* (2006.01)
*G06N 5/00* (2006.01)

(52) U.S. Cl. .............................. 706/50; 711/100; 707/3

(58) Field of Classification Search ........................ None
See application file for complete search history.

(56) References Cited

U.S. PATENT DOCUMENTS 7,126,467 B2* 10/2006 Albert et al. ................. 340/521
2006/0085393 A1* 4/2006 Modesitt ......................... 707/3
2006/0176182 A1* 8/2006 Noguchi et al. ........... 340/573.1

* cited by examiner

*Primary Examiner*—David R Vincent
*Assistant Examiner*—Kalpana Bharadwaj
(74) *Attorney, Agent, or Firm*—Hope Baldauff Hartman, LLC

(57) ABSTRACT

Methods and systems for gathering lifestyle-based Health, Safety and Security (HSS) risks and conducting associated analyses by collecting HSS information related to potential health risks, safety hazards, and security concerns existing at a client location. Product and service information relating to one or more products or services for mitigating or eliminating said potential health risks, safety hazards, or security concerns are automatically identified using the gathered HSS information, where the one or more products or services mitigate or eliminate the potential health risks, safety hazards or security concerns. Additionally, an order is automatically assembled for purchasing the one or more products or services based upon the potential health risks, safety hazards or security concerns.

30 Claims, 40 Drawing Sheets

PrepareFirst™
*Health & Safety Preparedness*

Friday, March 20, 2003 2:57 AM

Home Appointments Clients Reports Admin Exit

Client: Bob Samuelson
Phone: 756-098-7865

Appointment Date: 3/18/2003
Email: evilempire@starwars.com

Analysis Inspection

| Area | Hazards | Reviewed | Pending |
|---|---|---|---|
| 1st Floor Laundry Area | 46 | 2 | 44 |
| 3rd Floor Hallway (Beige) | 46 | 2 | 44 |
| 3rd Floor Bathroom (Brown) | 46 | 2 | 44 |
| 3rd Floor Dining Room (Beige) | 71 | 22 | 49 |
| 3rd Floor Hallway (Beige) | 71 | 22 | 49 |
| Garage Pool Area (Grey) | 20 | 0 | 20 |

Back    Add Room

PrepareFirst™
Health & Safety Preparedness

Home Appointments Clients Reports Admin Exit

Friday, March 20, 2003 2:29 AM

Indoor Areas

| | | | |
|---|---|---|---|
| ANY | Dining Room | General | Playroom |
| Basement | Door | Hallway | Pool Area |
| Bathroom | Electrical Fuse Box | Kitchen | Staircase |
| Bedroom | Entry Door | Laundry Area | Storage Room |
| Closet | Family Room | Living Room | Work Room |
| Closet in Bedroom | Foyer | Nursery | |
| Den | Garage | Office | |

Outdoor Areas

| | | | |
|---|---|---|---|
| Back Porch | Porch - Front Side | Roof Front | Yard - Left Side |
| Driveway | Porch - Left Side | Staircase | Yard - Right Side |
| Mailbox | Porch - Right Side | Storage Room | |
| Patio | Roof - Left Side | Work Room | |
| Porch | Roof - Right Side | Yard - Back | |
| Porch - Back Side | Roof Back | Yard - Front Side | |

[Go Back]

PrepareFirst™
Health & Safety Preparedness

Wednesday, April 8, 2003 11:40 AM

Home  Appointments  Clients  Reports  Admin  Exit

| Location | Sub Location | Hazard | Status | Rationale | Recommendation |
|---|---|---|---|---|---|
| 1st Floor | Bedroom | Exterior Entry Point - Roof, Crawl Space, Vent, e | Not protected against unlawful entry. | Risk of unlawful entry. | Install appropriate safeguard. |
| 1st Floor | Bedroom | Fabric (Curtains, Towel Rack, potholders, etc.) | Dangerous Location. | Risk of fire. | Remove OR relocate item. |
| 1st Floor | Bedroom | Fuel Burning Device (Fireplace, Heater, etc.) | "old, painted, and potentially dangerous." | | |
| 1st Floor | Bedroom | Fuel Burning Device (Fireplace, Heater, etc.) | "Worn, cracked, or frayed." | | |
| 1st Floor | Bedroom | Fuel Burning Device (Fireplace, Heater, etc.) | Able to be opened by child. | | |
| 1st Floor | Bedroom | Fuel Burning Device (Fireplace, Heater, etc.) | Accessible to children. | | |
| 1st Floor | Bedroom | Fuel Burning | | | |

HEALTH, SAFETY AND SECURITY ANALYSIS AT A CLIENT LOCATION

RELATED APPLICATION DATA

The present application claims priority to U.S. Provisional Patent Application Ser. No. 60/679,602, filed on May 10, 2005, titled "SYSTEMS, METHODS AND COMPUTER PROGRAM PRODUCTS FOR LIFESTYLE-BASED HEALTH, SAFETY AND SECURITY ANALYSIS", the entire contents of which are incorporated herein by reference as if set forth fully-herein.

FIELD OF THE INVENTION

The present invention relates to safety, and more particularly to systems, methods, and computer program products for gathering and conducting lifestyle-based analyses, identifying potential safety hazards, and automatically identifying one or more products or services for mitigating said potential safety hazards.

SUMMARY OF THE INVENTION

According to an embodiment of the invention, there is disclosed a computer program product for use with a data processing system for gathering and conducting lifestyle-based analyses. The computer program product includes a computer usable medium having computer-readable code means embodied in said medium, said computer-readable code means including computer readable program code means for receiving safety information input into said computer program product, computer readable program code means for evaluating said safety information to identify safety hazards, and computer readable program code means for recommending, based upon said safety hazards, one or more products or services to mitigate or eliminate said safety hazards.

According to an aspect of the invention, the computer usable medium further includes computer-readable code means for receiving security information input into said computer program product. The computer usable medium can further include computer-readable code means for evaluating said security information to identify security hazards, and/or computer-readable code means for recommending, based upon said security hazards, one or more products or services to mitigate or eliminate said security hazards. According to another aspect of the invention, the computer-readable code means include means for receiving health information input into said computer program product.

According to yet another aspect of the invention, the computer usable medium further includes computer-readable code means for evaluating said health information to identify health hazards. The computer usable medium may further include computer-readable code means for recommending, based upon said health hazards, one or more products or services to mitigate or eliminate said health hazards. The computer usable medium may be accessible via a Wide Area Network (WAN). Further, the computer program product may include a software program, and the computer program product may reside on a device selected from devices consisting of a laptop computer, a server, a personal computer, a personal digital assistant, a hand held computer, and a portable computer.

According to another embodiment of the invention, there is disclosed a method for conducting lifestyle-based analyses. The method includes collecting safety information related to potential safety hazards existing at a client location, gathering product and service information, where the product and service information relates to one or more products or services for mitigating said potential safety hazards, and automatically identifying, using said safety information, the one or more products or services for mitigating said potential safety hazards.

According to one aspect of the invention, the method includes collecting security information related to potential security hazards existing at a client location. Gathering may further include the step of gathering product and service information relating to one or more products or services for mitigating said potential security hazards, and the step of automatically identifying may further include automatically identifying, using the security information, the one or more products or services for mitigating said potential security hazards. According to another aspect of the invention, the method includes collecting health information related to potential health hazards of a client. According to yet another aspect of the invention, the step of gathering includes the step of gathering product and service information relating to one or more products or services for mitigating said potential health hazards, and the step of automatically identifying further includes automatically identifying, using the health information, the one or more products or services for mitigating said potential health hazards.

The method may also include monitoring a client profile and using the profile to automatically identify the one or more products or services for mitigating the potential health hazards. The method may further include monitoring a client profile and using the profile to automatically identify the one or more products or services for mitigating the potential safety hazards. According to another aspect of the invention, the method can include monitoring a client profile and using the profile to automatically identify the one or more products or services for mitigating the potential security hazards. The method may additionally include generating a score comparing a client's preparedness in relation to a standard determined using at least one reference selected from references consisting of public accident statistics, disaster statistics, injury statistics, health statistics and/or other statistics or information.

According to another embodiment of the invention, there is disclosed a system for gathering and conducting lifestyle-based analyses. The system includes at least one input device, the at least one input device operable to receive data related to health, safety and/or security hazards. The system also includes at least one storage medium, in communication with the at least one input device, the at least one storage medium configurable to store the data related to client specific health, safety and/or security hazards, and at least one program, the at least one program operable to analyze data related to client specific health, safety and/or security hazards and to generate product and/or service recommendations to mitigate or eliminate the client specific health, safety and/or security hazards.

According to an aspect of the invention, the at least one input device is in remote communication with the at least one storage medium. The at least one input device and the at least one storage medium may be in communication via the Internet. According to another aspect of the invention, the at least one program is in remote communication with the at least one input device. The at least one program may further be operable to generate quotes and/or estimates of services and/or products corresponding to the product and/or service recommendations to mitigate or eliminate the health, safety and/or security hazards. According to yet another aspect of the invention, the system may further include an output device, the output device operable to display the product and/or service recommendations to mitigate or eliminate the health, safety and/or security hazards.

According to another aspect of the invention, the quote and/or estimates generated are displayed via an output device. Moreover, the at least one program may be operable to track the expiration dates of the products corresponding to the product recommendations to mitigate or eliminate the health, safety and/or security hazards, and/or may be operable to identify when the expiration dates of such products have expired. The program may further be operable to compare the product and/or service recommendations.

According to yet another embodiment of the invention, there is disclosed a method for gathering lifestyle-based health, safety and security risks and conducting associated analyses. The method includes collecting, at a client location or over the Internet, health, safety, and security information related to potential health risks, safety hazards, and security concerns existing at a client location, and gathering product, service, and behavioral modification information, where the product, service, and suggested behavioral modification information relates to one or more products or services for mitigating or eliminating the potential health risks, safety hazards, or security concerns. The method further includes automatically identifying, using the safety information, the one or more products, services, and suggested behavioral modifications for mitigating or eliminating the potential health risks, safety hazards or security concerns, and automatically assembling an order for purchasing the one or more products or services based upon the potential health risks, safety hazards or security concerns.

BRIEF DESCRIPTION OF THE DRAWINGS

Figure 1:
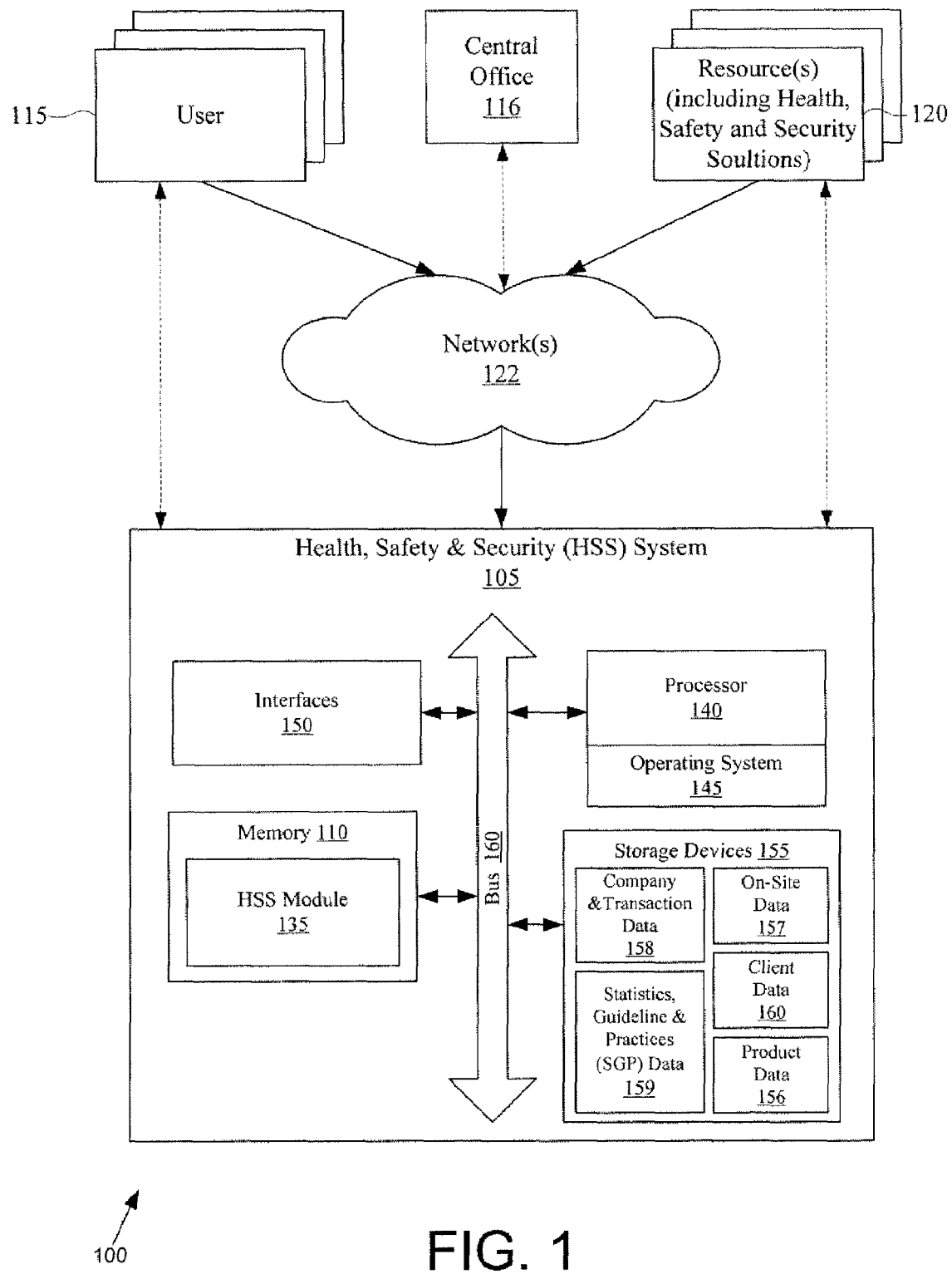

Having thus described the invention in general terms, reference will now be made to the accompanying drawings, which are not necessarily drawn to scale, and wherein:

FIG. 1 shows a system, in block diagram form, for identifying health, safety & security hazards and identifying solutions, according to an embodiment of the present invention.

Figure 2:
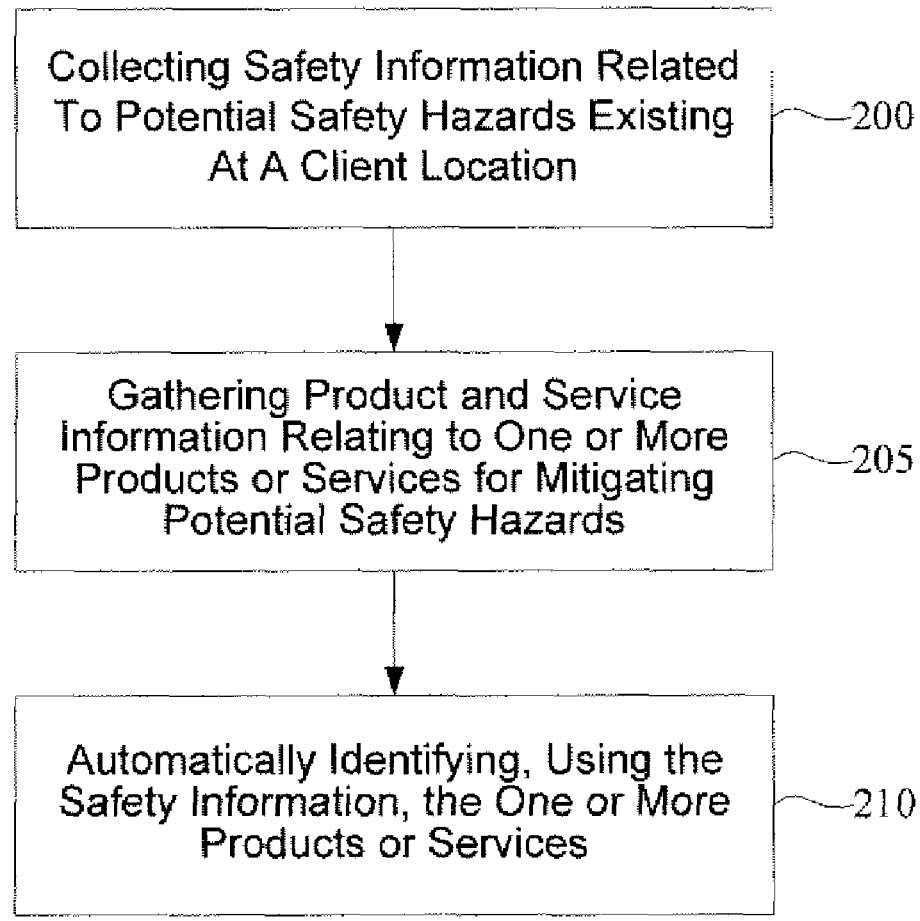

FIG. 2 is a block diagram flow chart illustrating a risk assessment and solution identification process performed in accordance with an illustrative embodiment of the present invention.

Figure 3:
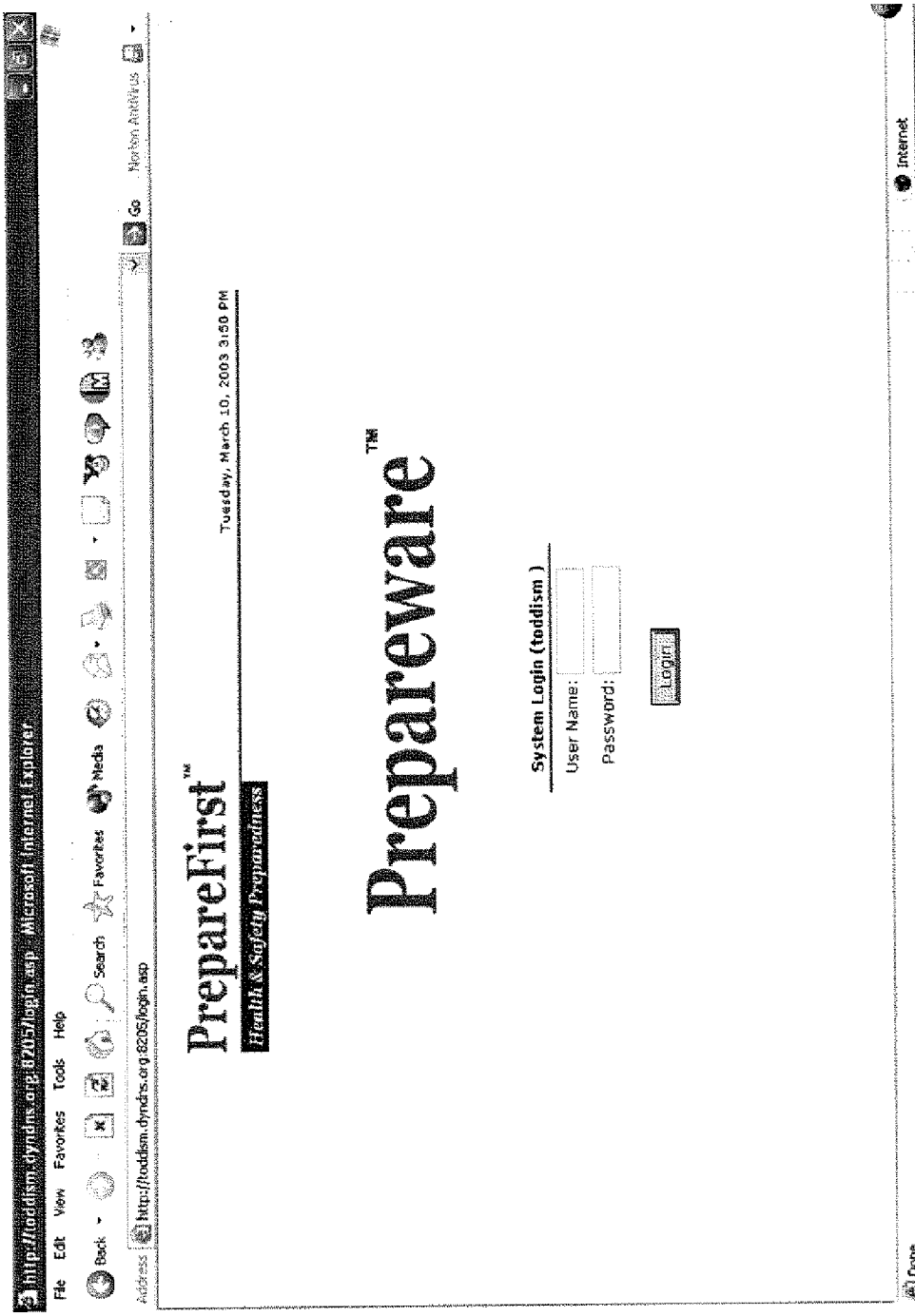

FIG. 3 shows a system and data security GUI, according to an illustrative example and exemplary embodiment of the present invention.

FIG. 4 shows an appointment GUI, according to an illustrative example and exemplary embodiment of the present invention.

Figure 5:
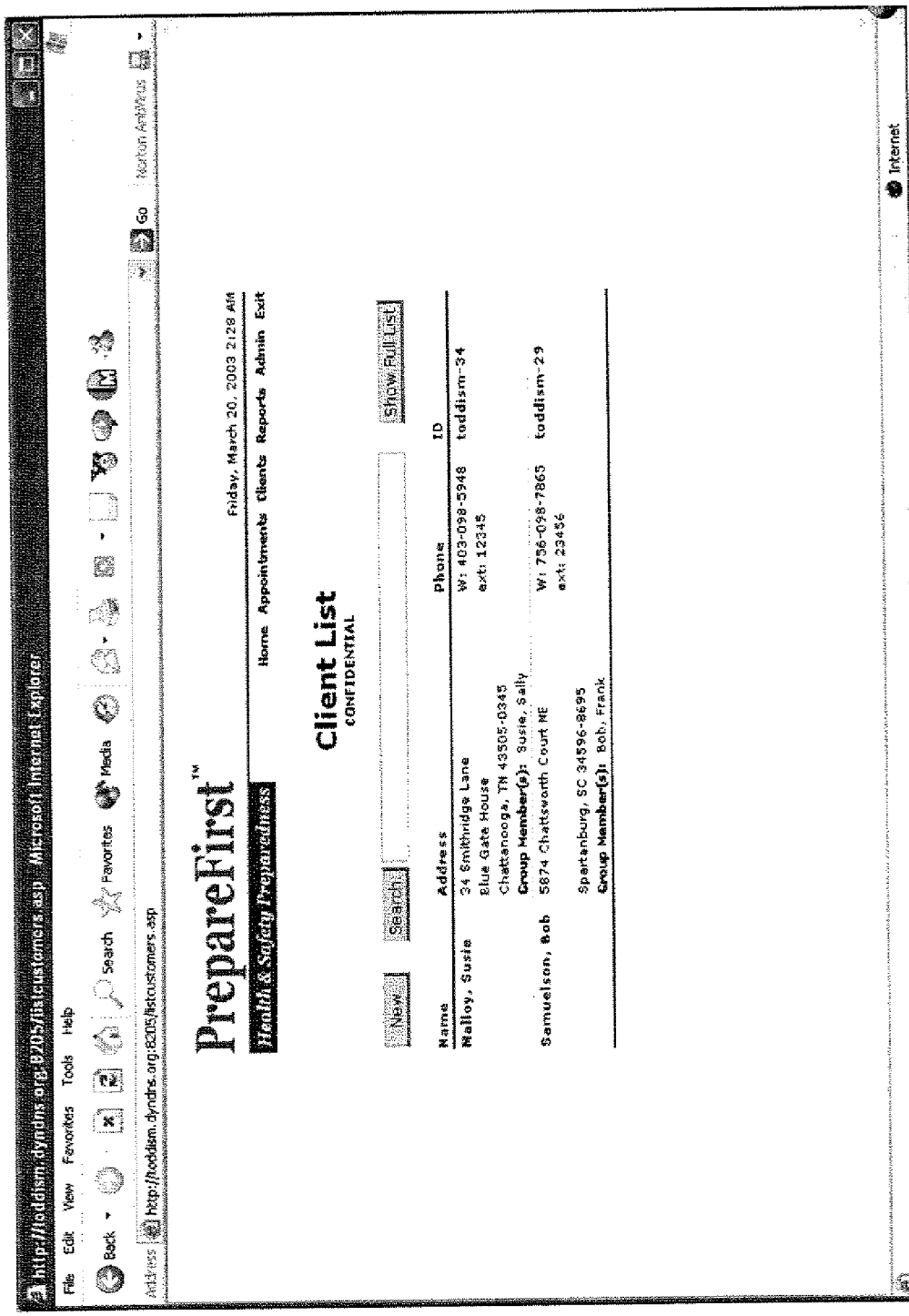

FIG. 5 shows a client identification GUI, according to an illustrative example and exemplary embodiment of the present invention.

Figure 6:
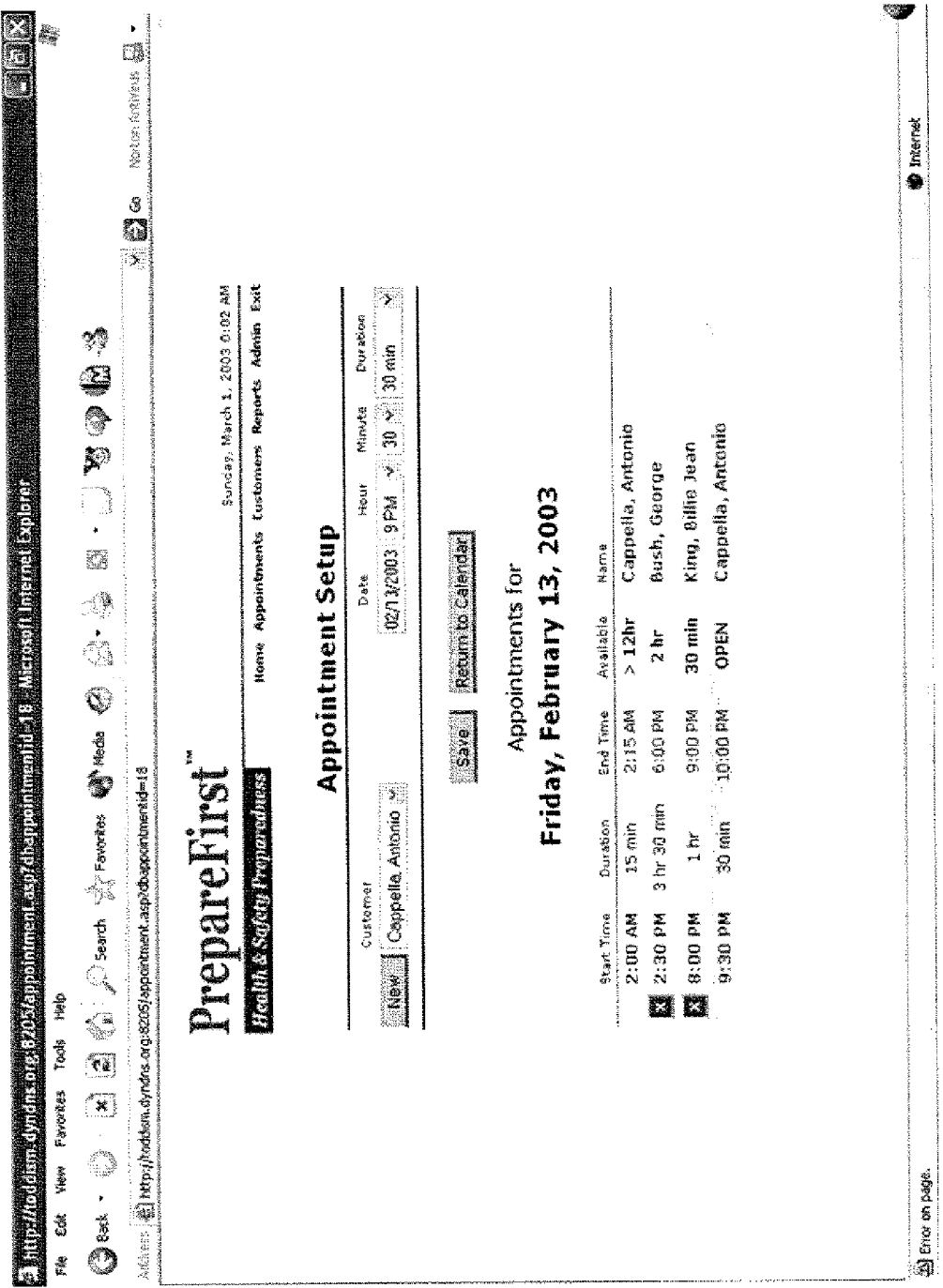

FIG. 6 shows an appointment setup GUI, according to an illustrative example and exemplary embodiment of the present invention.

FIG. 7 shows a client service agenda GUI, according to an illustrative example and exemplary embodiment of the present invention.

Figure 8:
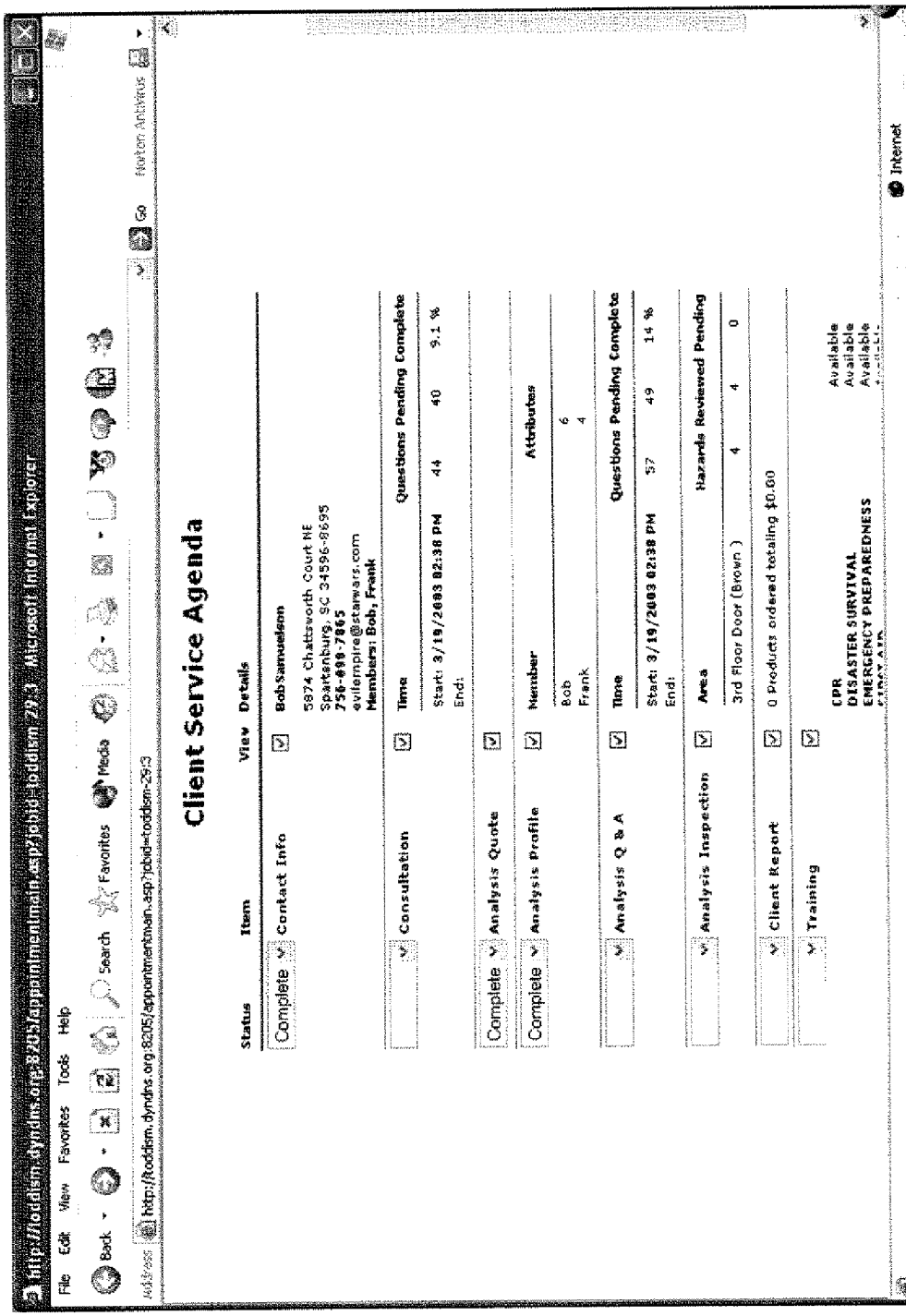

FIG. 8 shows a second view of a client service agenda GUI, according to an illustrative example and exemplary embodiment of the present invention.

FIG. 9 shows a second view of a client service agenda GUI, according to an illustrative example and exemplary embodiment of the present invention.

Figure 10:
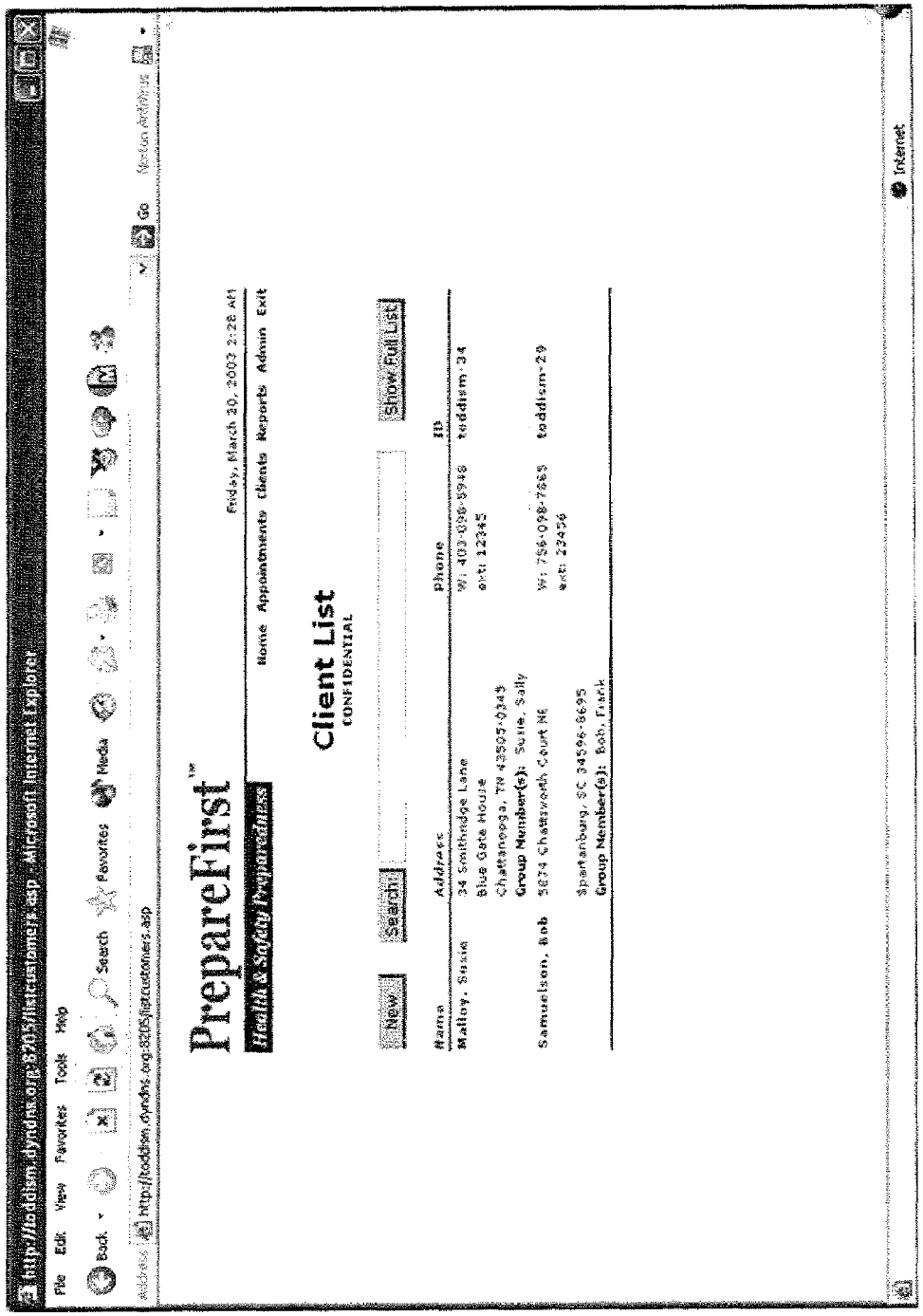

FIG. 10 shows a client list GUI, according to an illustrative example and exemplary embodiment of the present invention.

Figure 11:
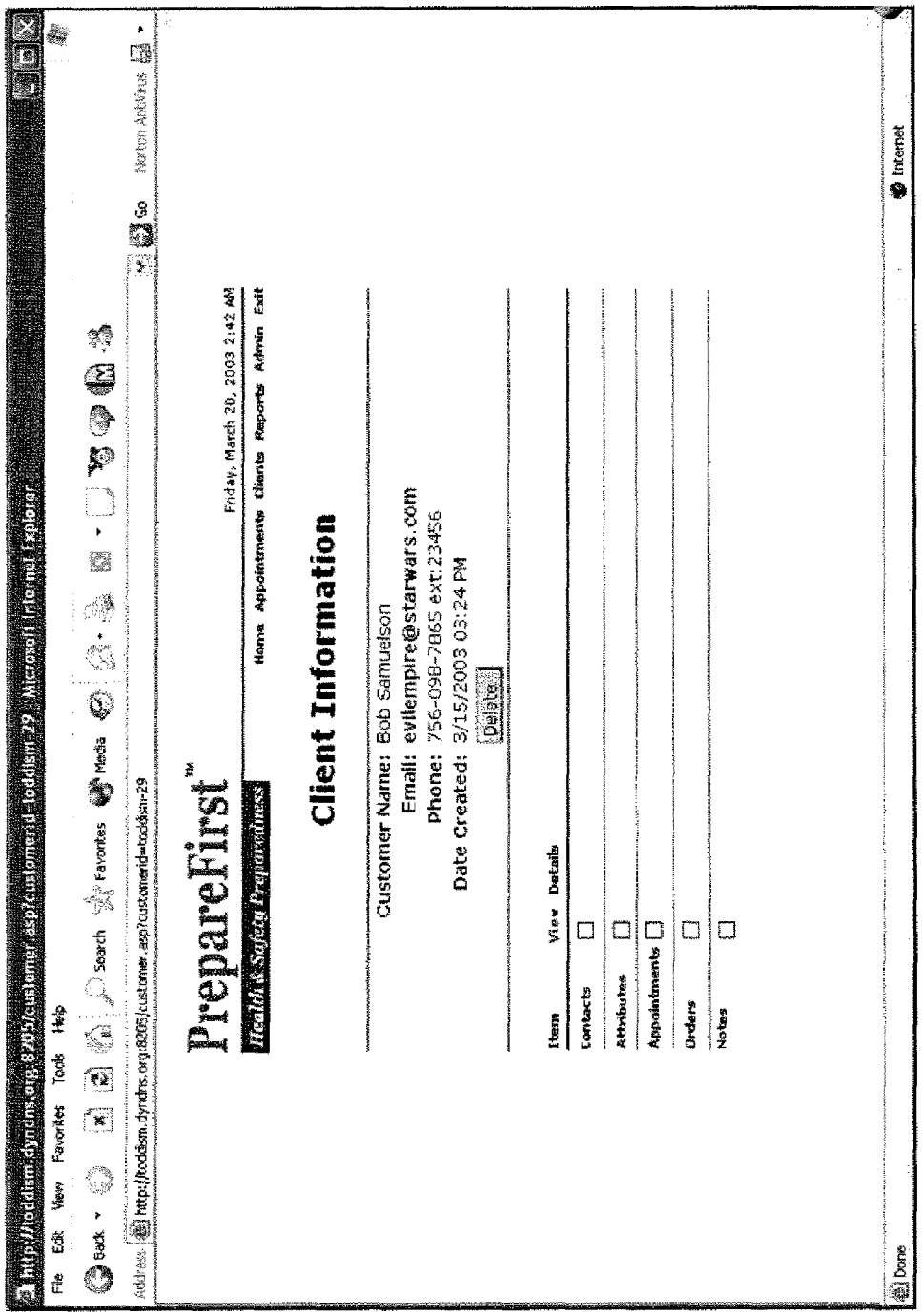

FIG. 11 shows a client record GUI, according to an illustrative example and exemplary embodiment of the present invention.

FIG. 12 shows a consultation GUI, according to an illustrative example and exemplary embodiment of the present invention.

Figure 13:
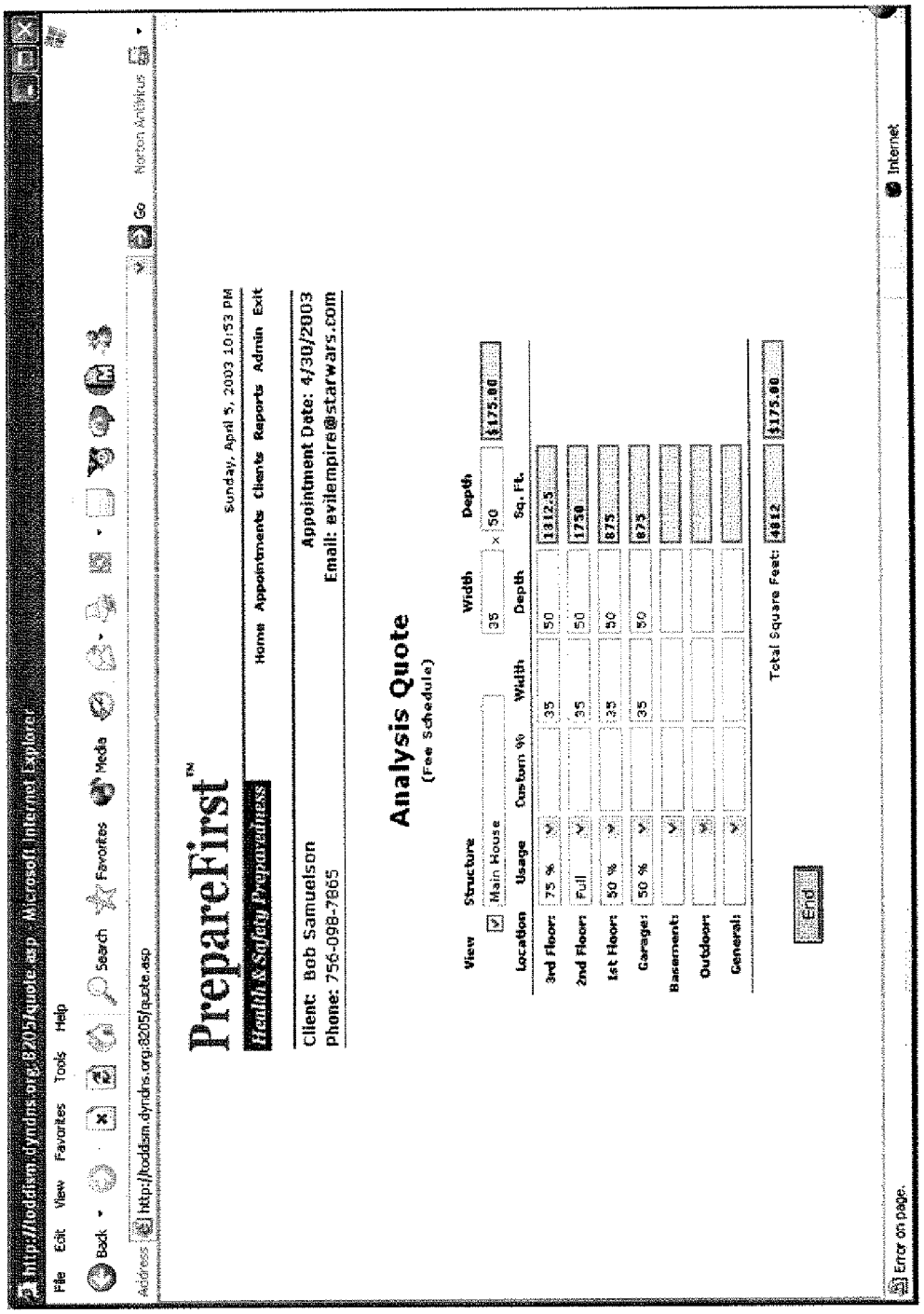

FIG. 13 shows an analysis quote GUI, according to an illustrative example and exemplary embodiment of the present invention.

FIG. 14 shows an attribute association GUI, according to an illustrative example and exemplary embodiment of the present invention.

Figure 15:
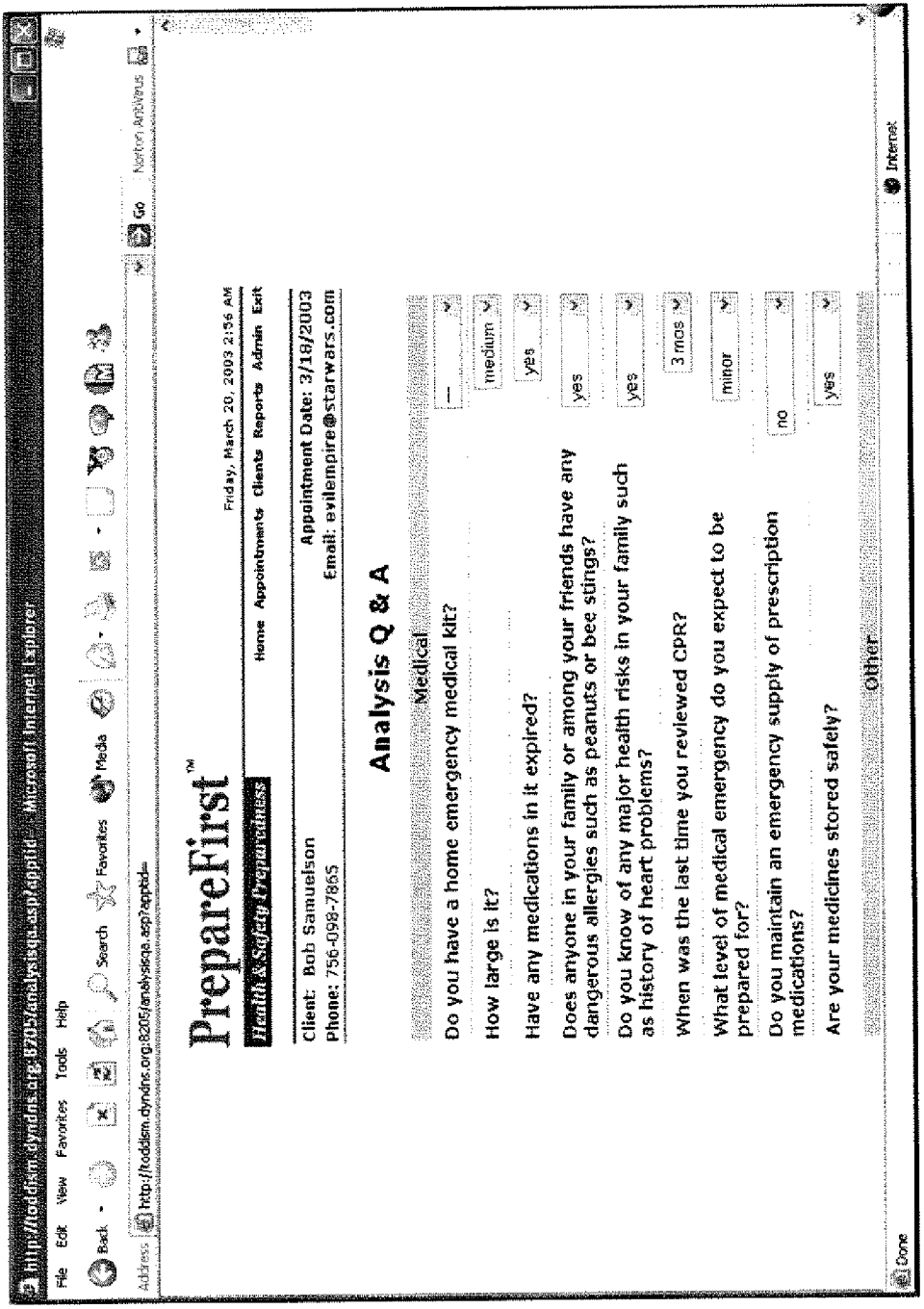
Figure 17:
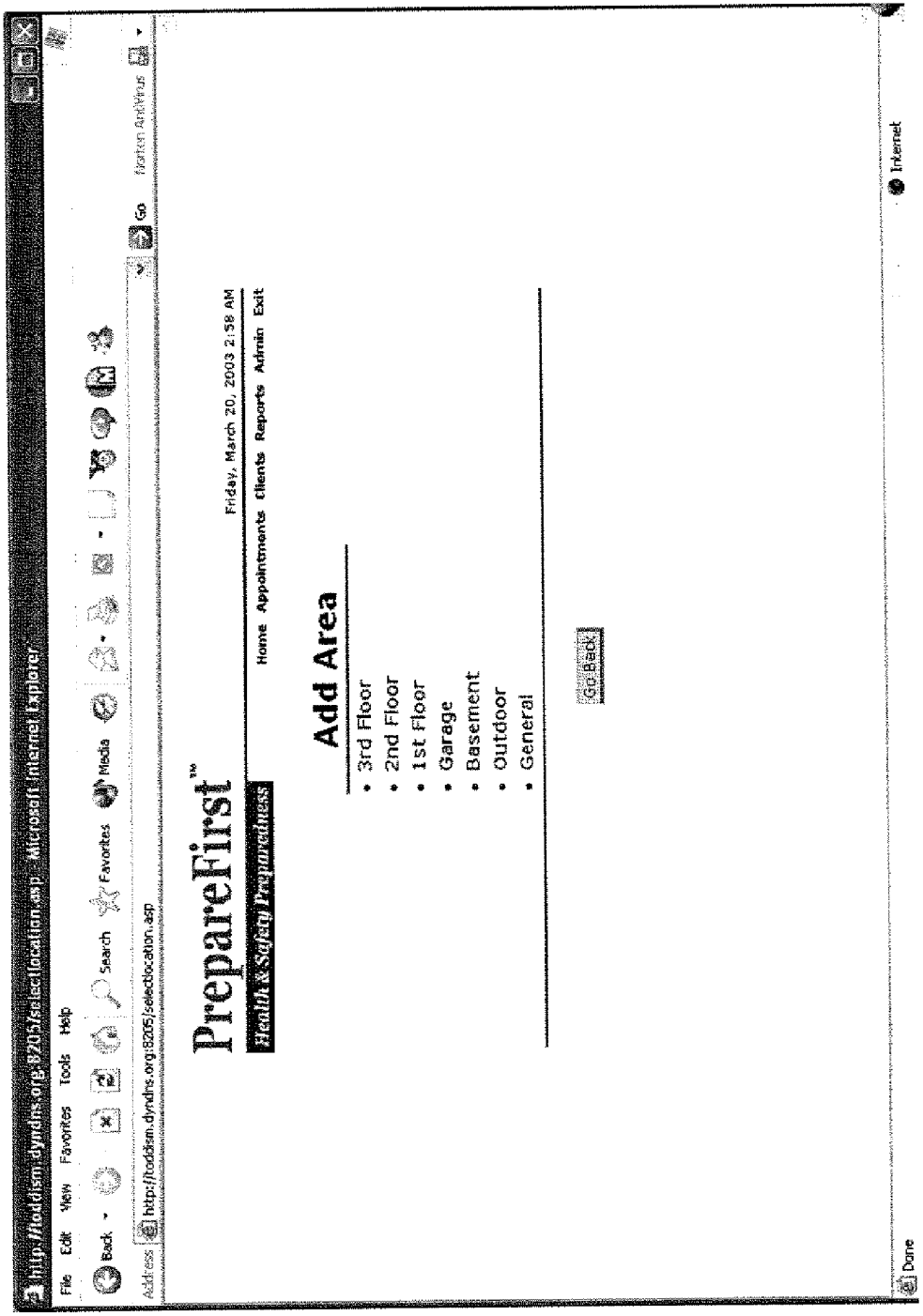
Figure 19:
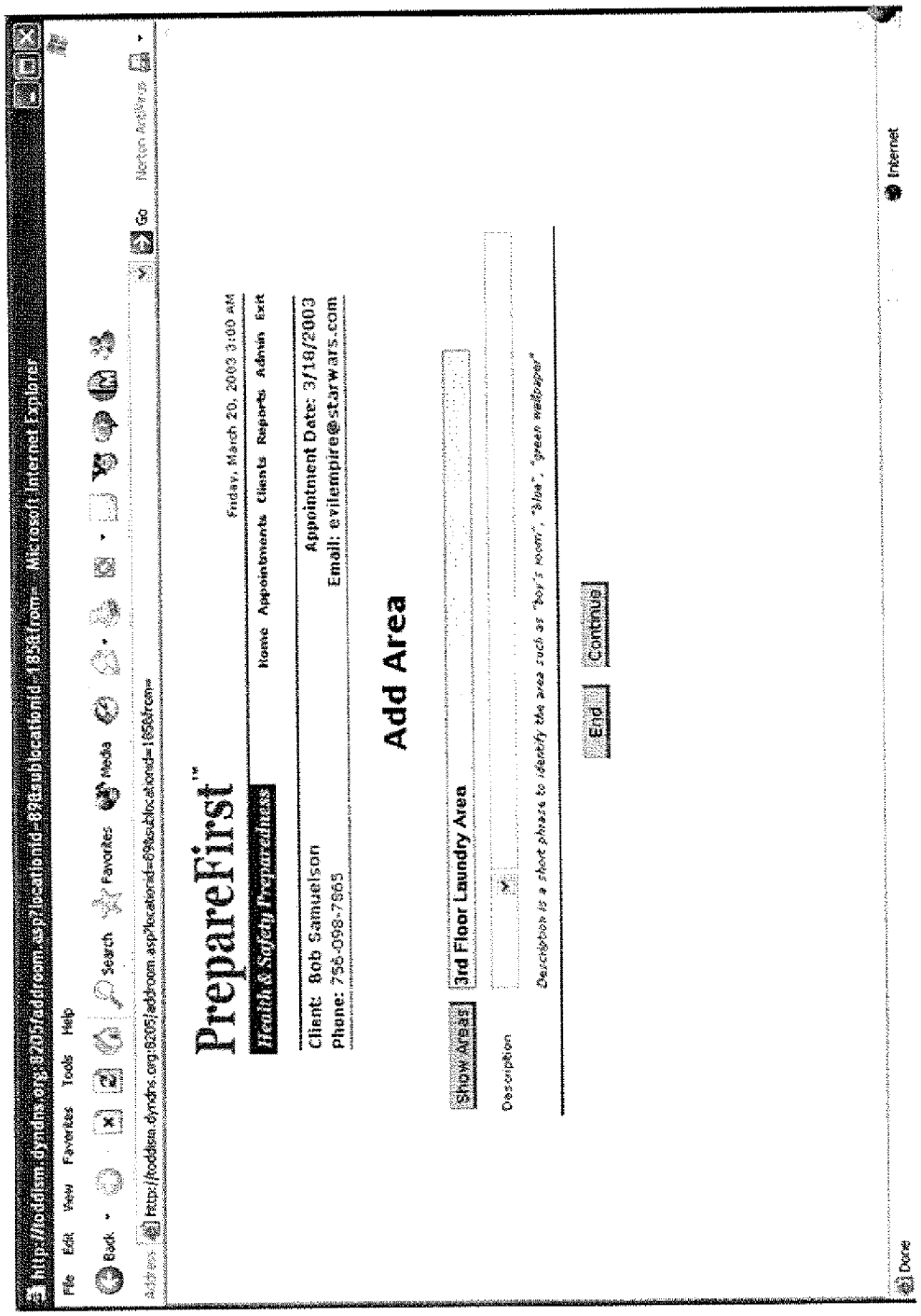

FIG. 15 shows an analysis question and answer GUI, according to an illustrative example and exemplary embodiment of the present invention.

FIGS. 16-19 show analysis inspection process GUIs according to illustrative examples and exemplary embodiments of the present invention.

Figure 20:
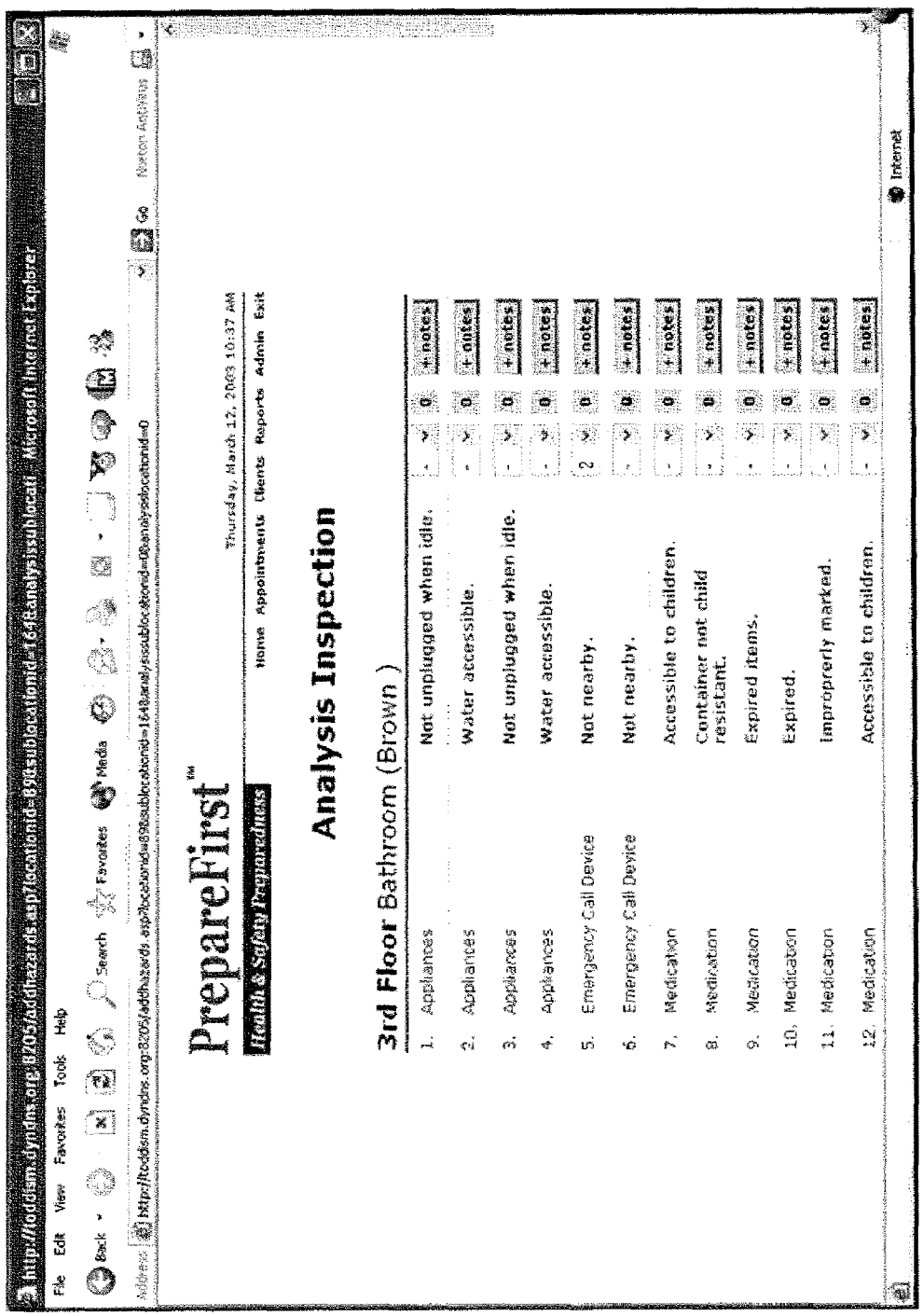

FIG. 20 shows an analysis inspection GUI, according to an illustrative example and exemplary embodiment of the present invention.

Figure 22:
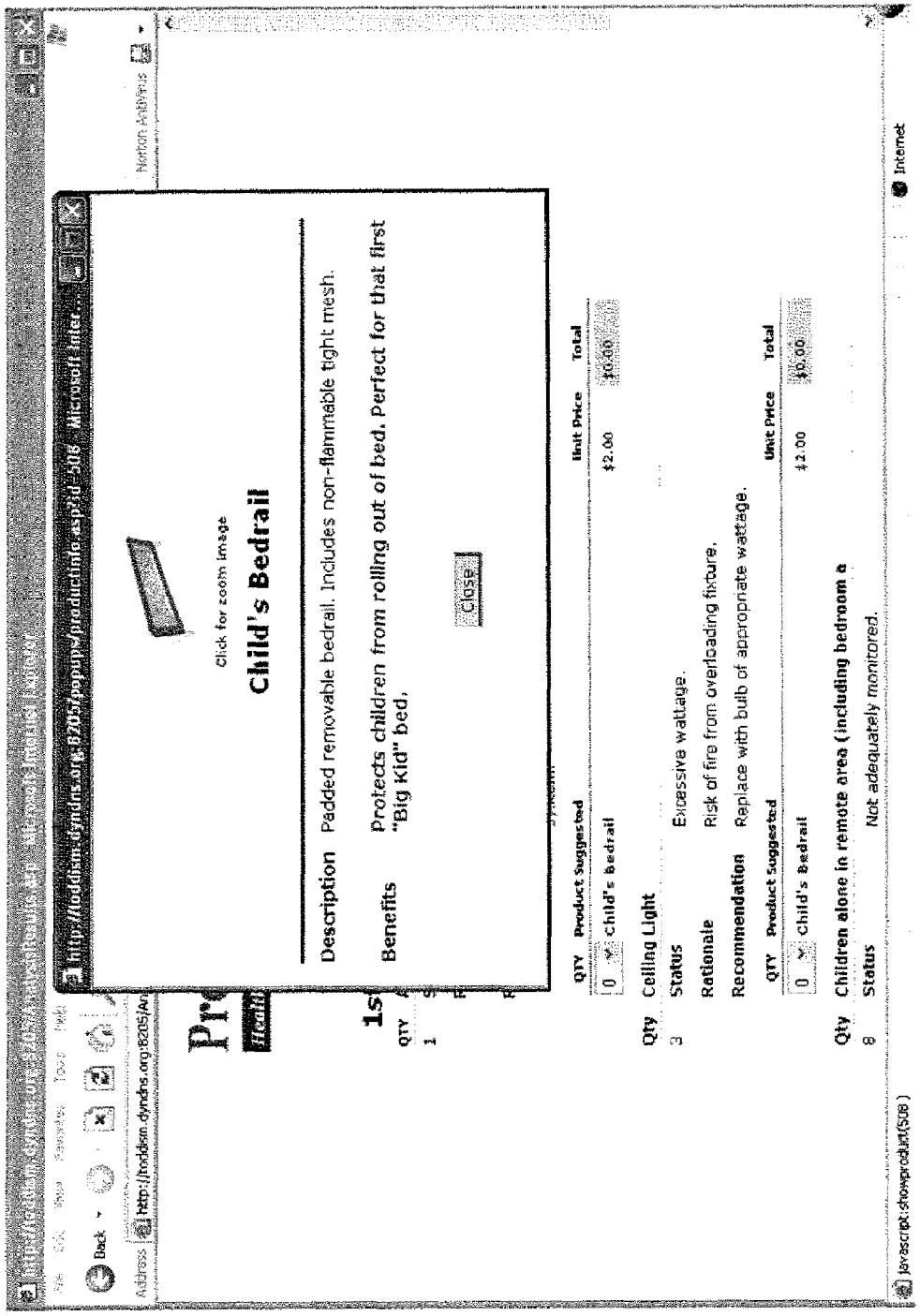

FIGS. 21 and 22 show client report GUIs, according to illustrative examples and exemplary embodiments of the present invention.

Figure 23:
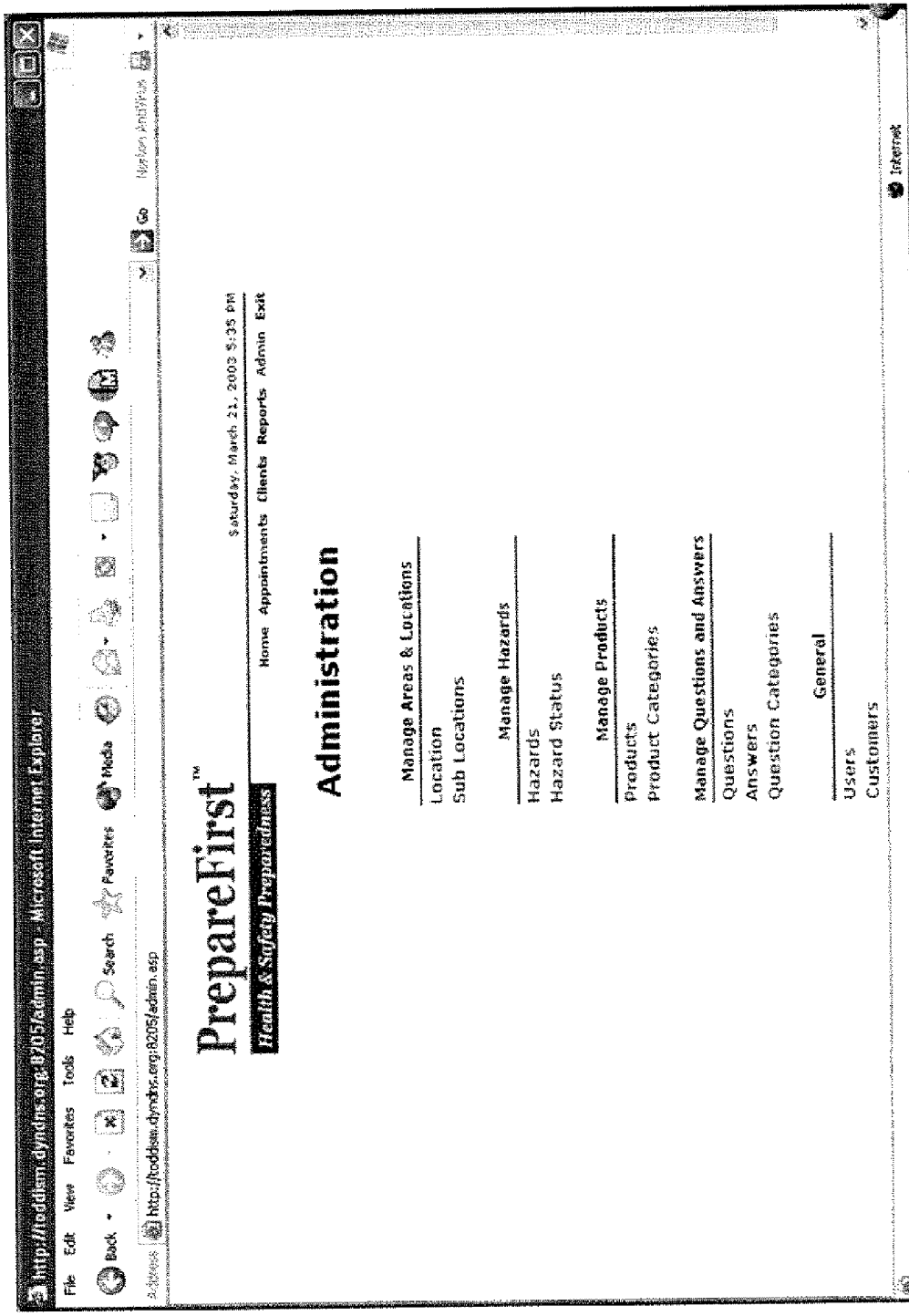

FIG. 23 shows an administration GUI, according to an illustrative example and exemplary embodiment of the present invention.

Figure 24:
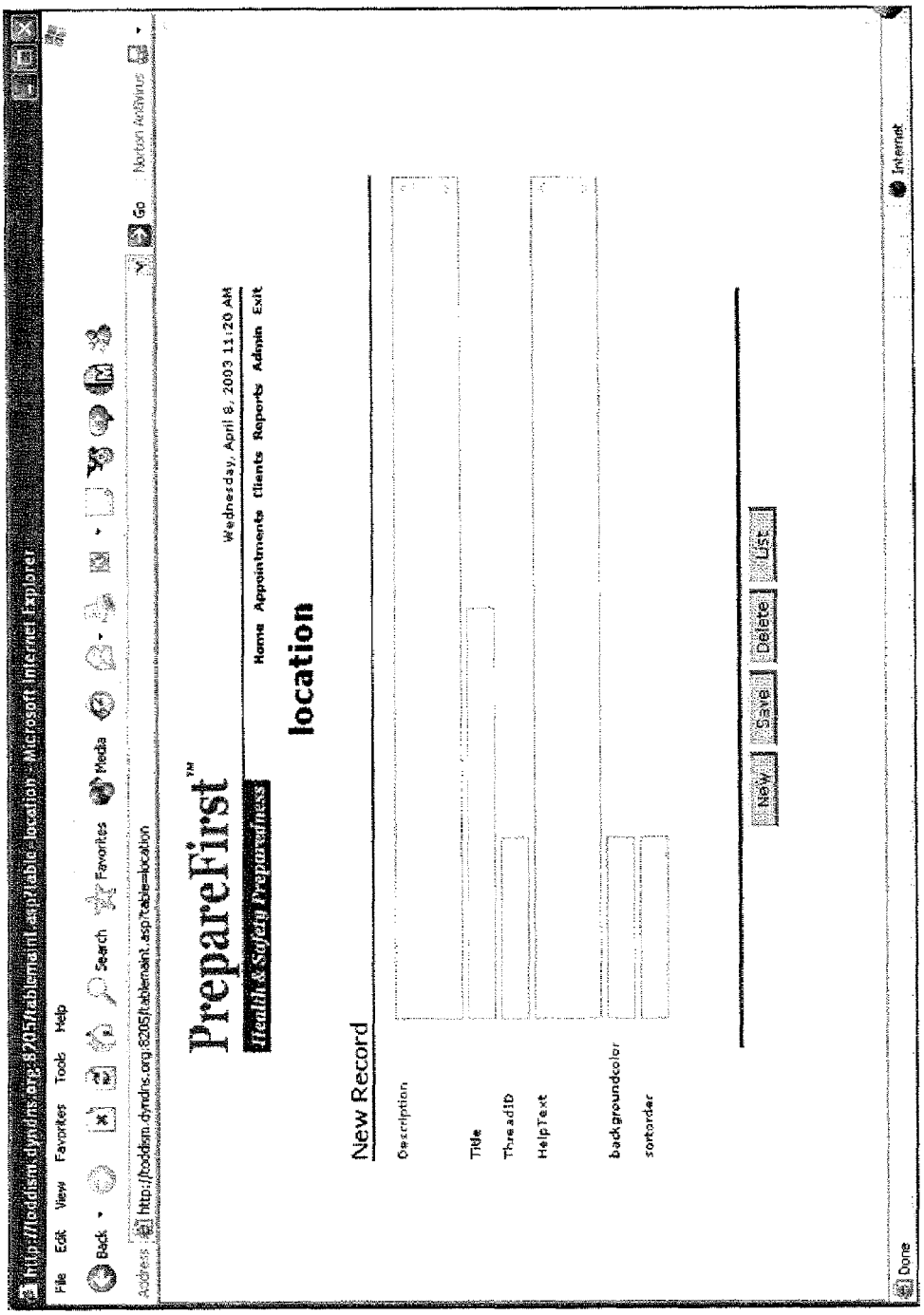
Figure 25:
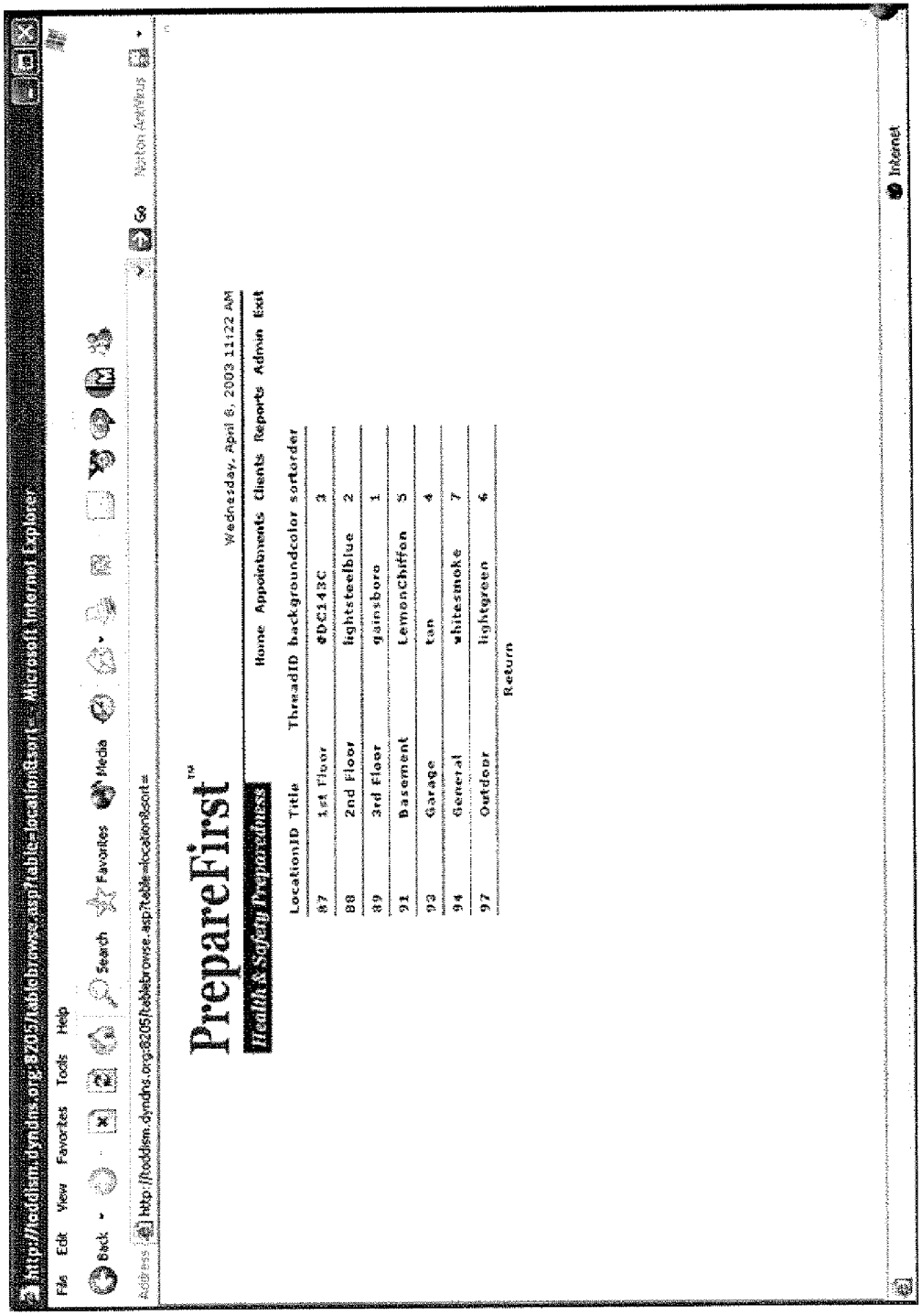

FIGS. 24 and 25 show definition of area GUIs, according to illustrative examples and exemplary embodiments of the present invention.

Figure 26:
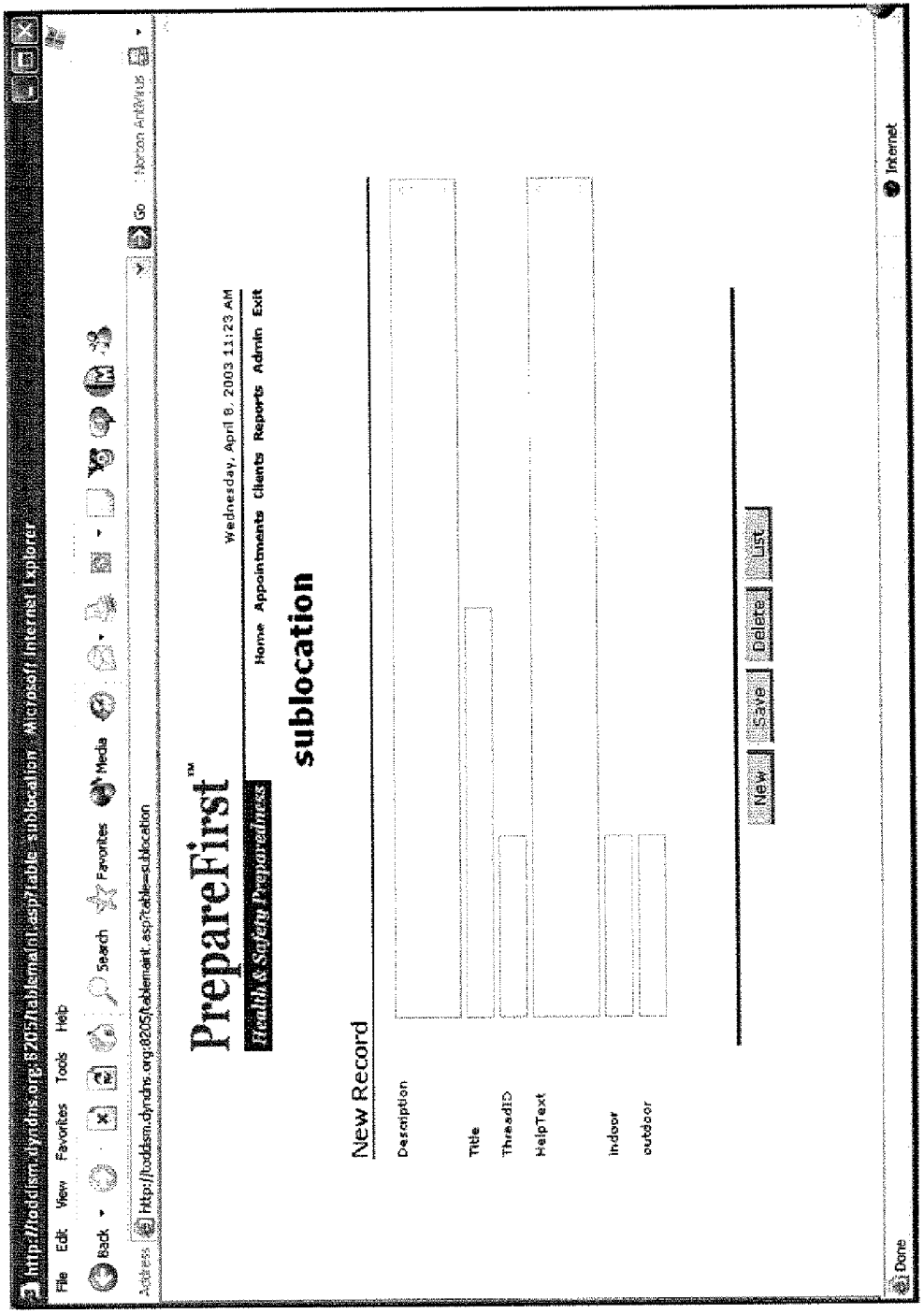
Figure 27:
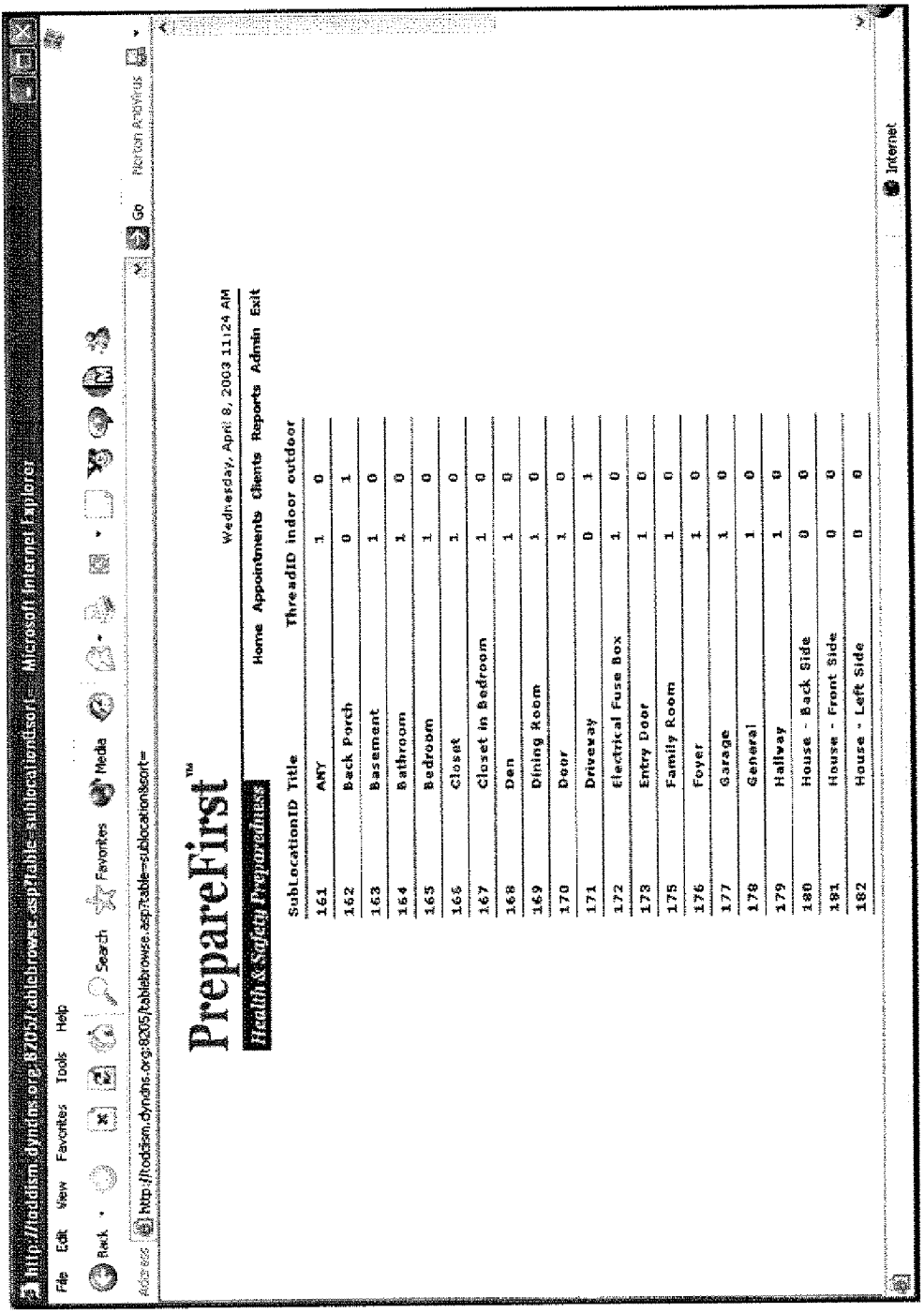

FIGS. 26 and 27 show definition of subarea GUIs, according to illustrative examples and exemplary embodiments of the present invention.

FIGS. 28-30 shows a hazard definition and association GUIs, according to illustrative examples and exemplary embodiments of the present invention.

Figure 31:
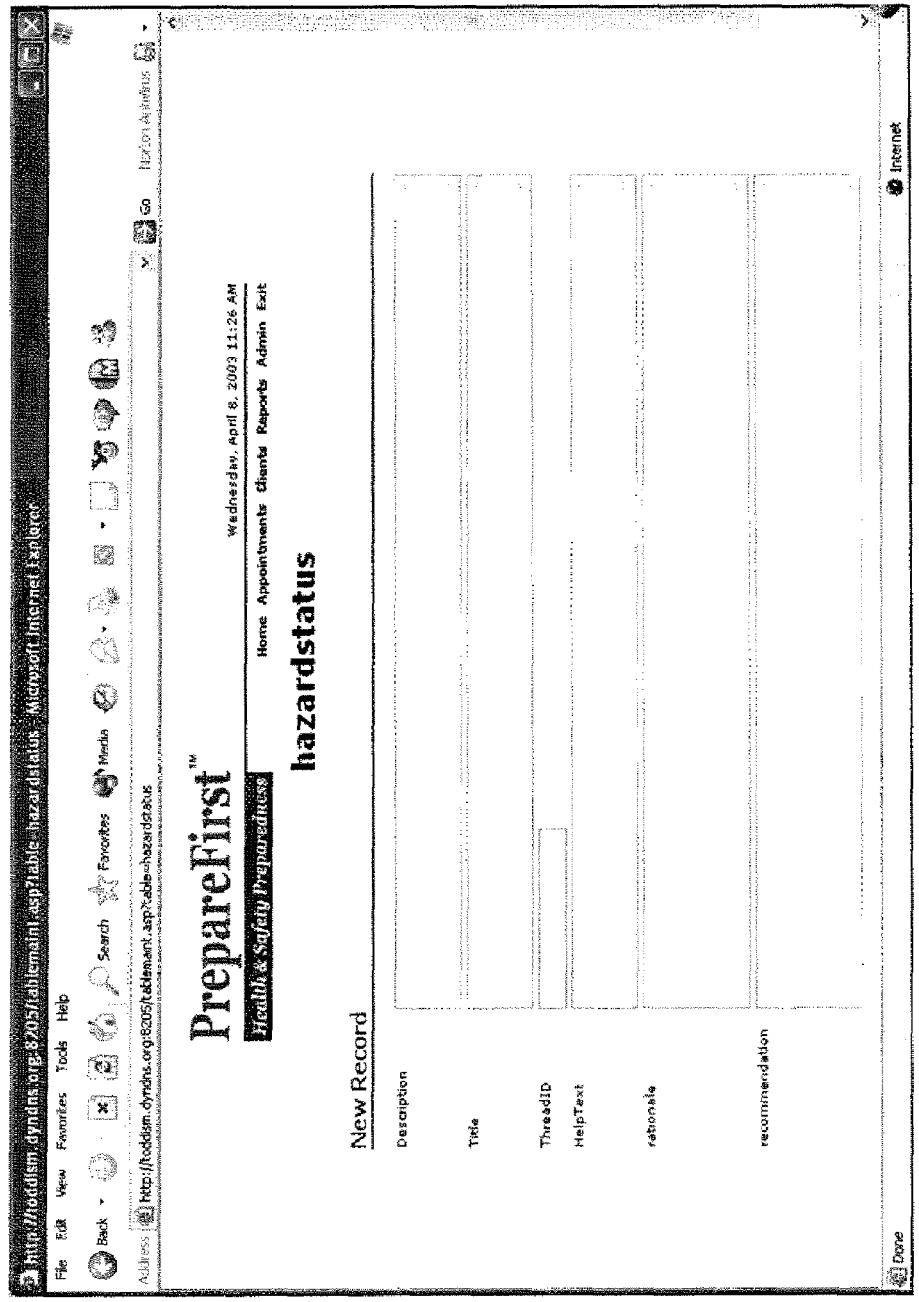
Figure 32:
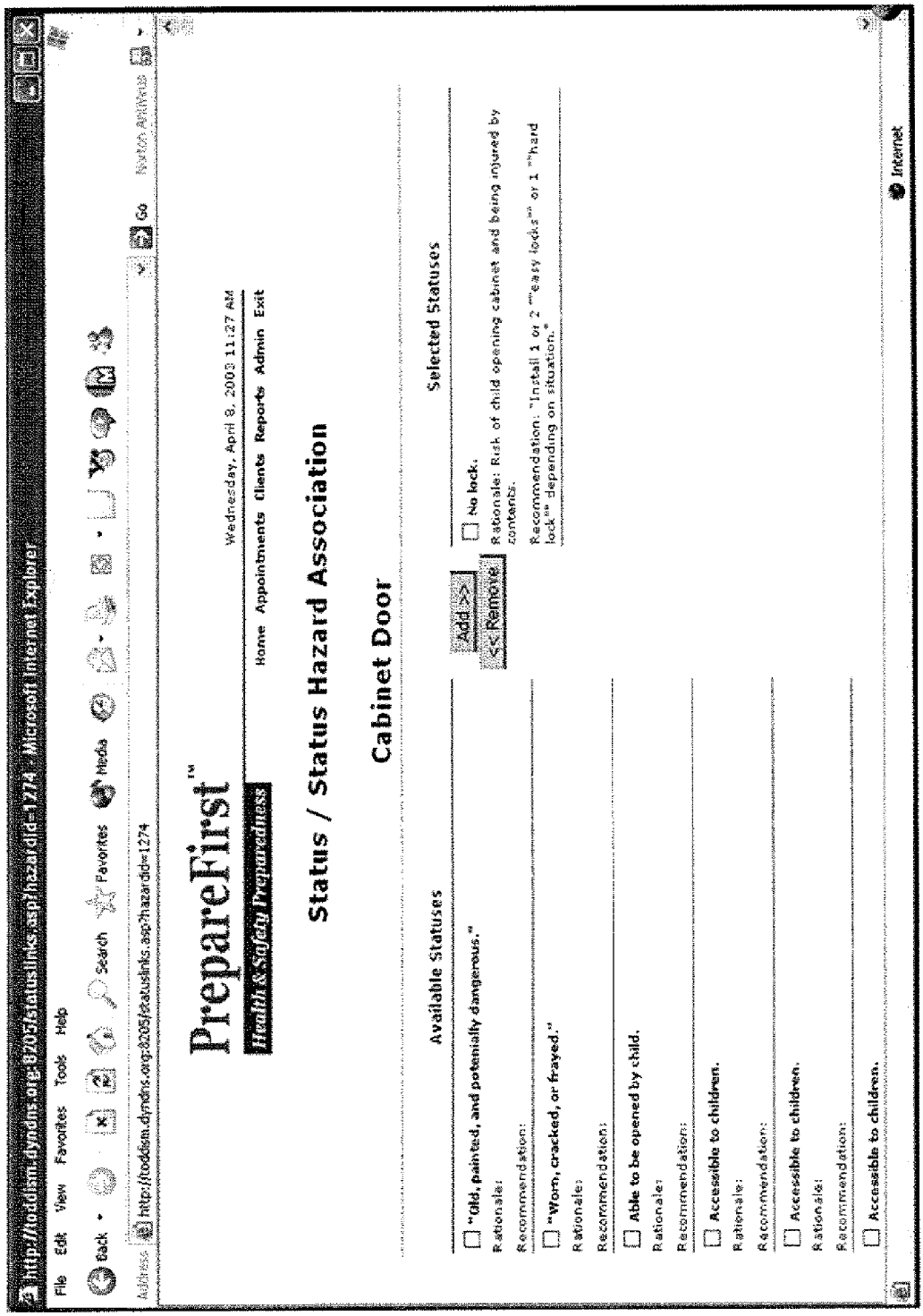

FIGS. 31-32 show a hazard status and detailed hazard association GUIs, according to illustrative examples and exemplary embodiments of the present invention.

Figure 33:
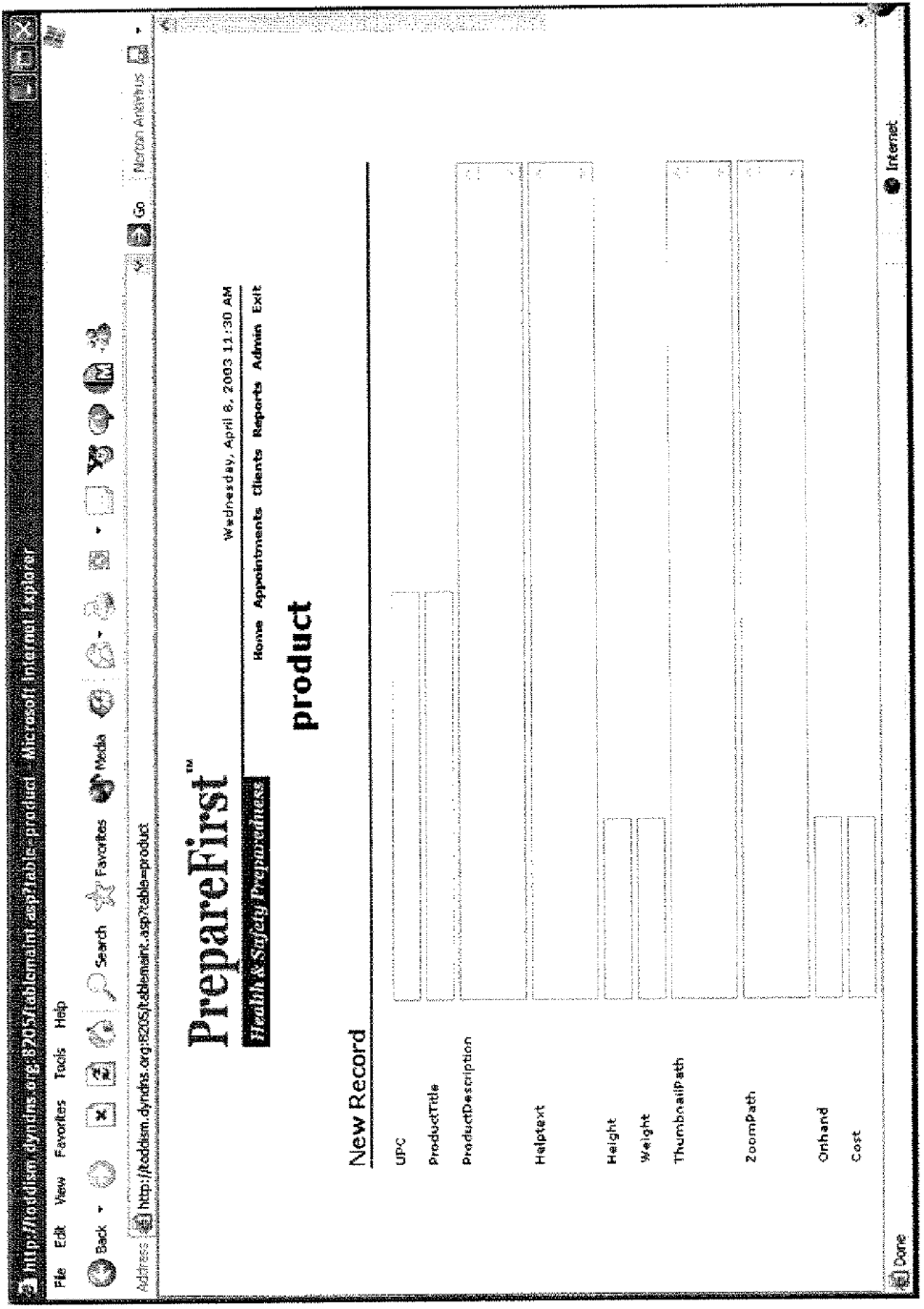
Figure 34:
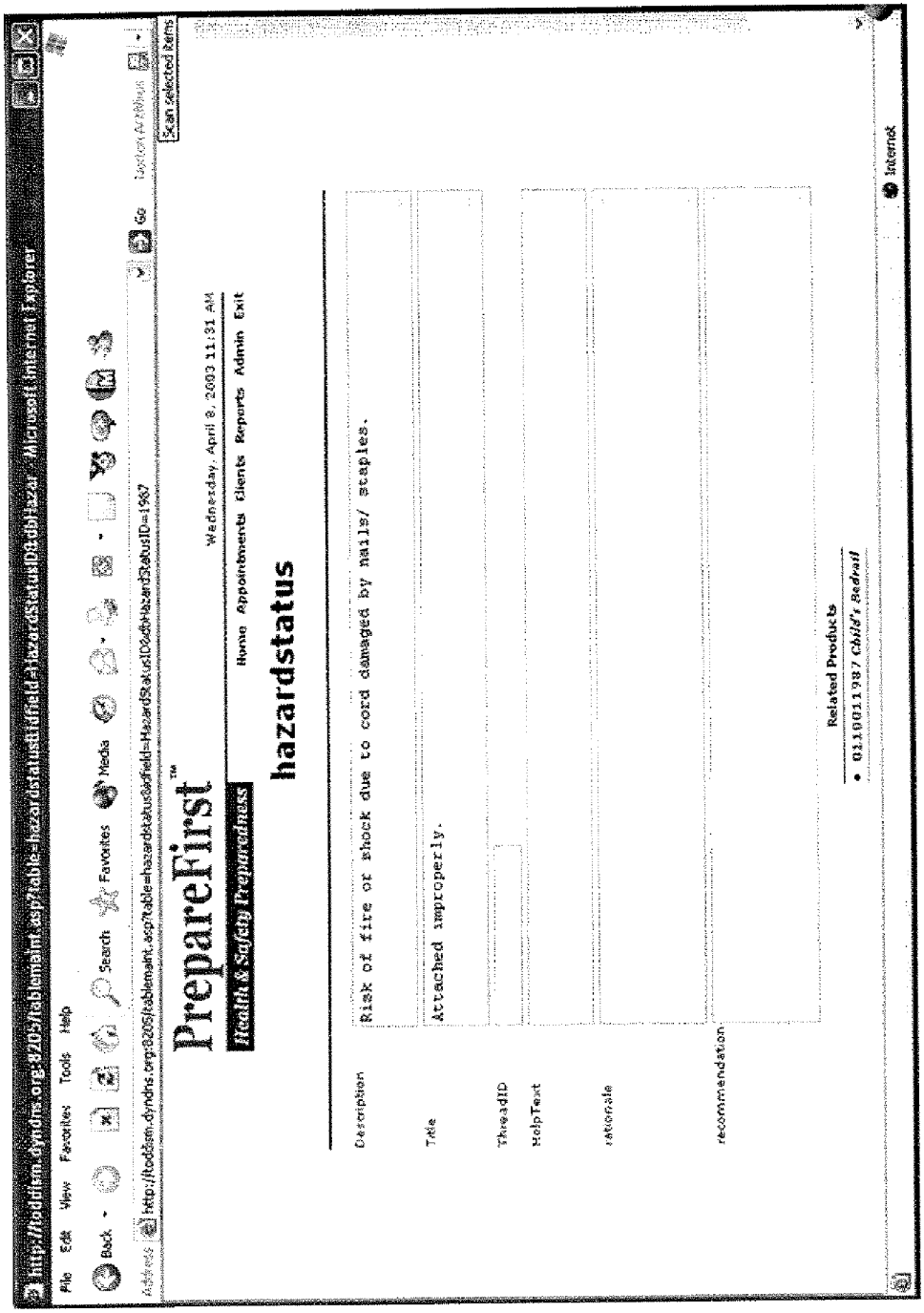

FIGS. 33-34 show product and sublocation hazard status GUIs, respectively, according to illustrative examples and exemplary embodiments of the present invention.

Figure 35:
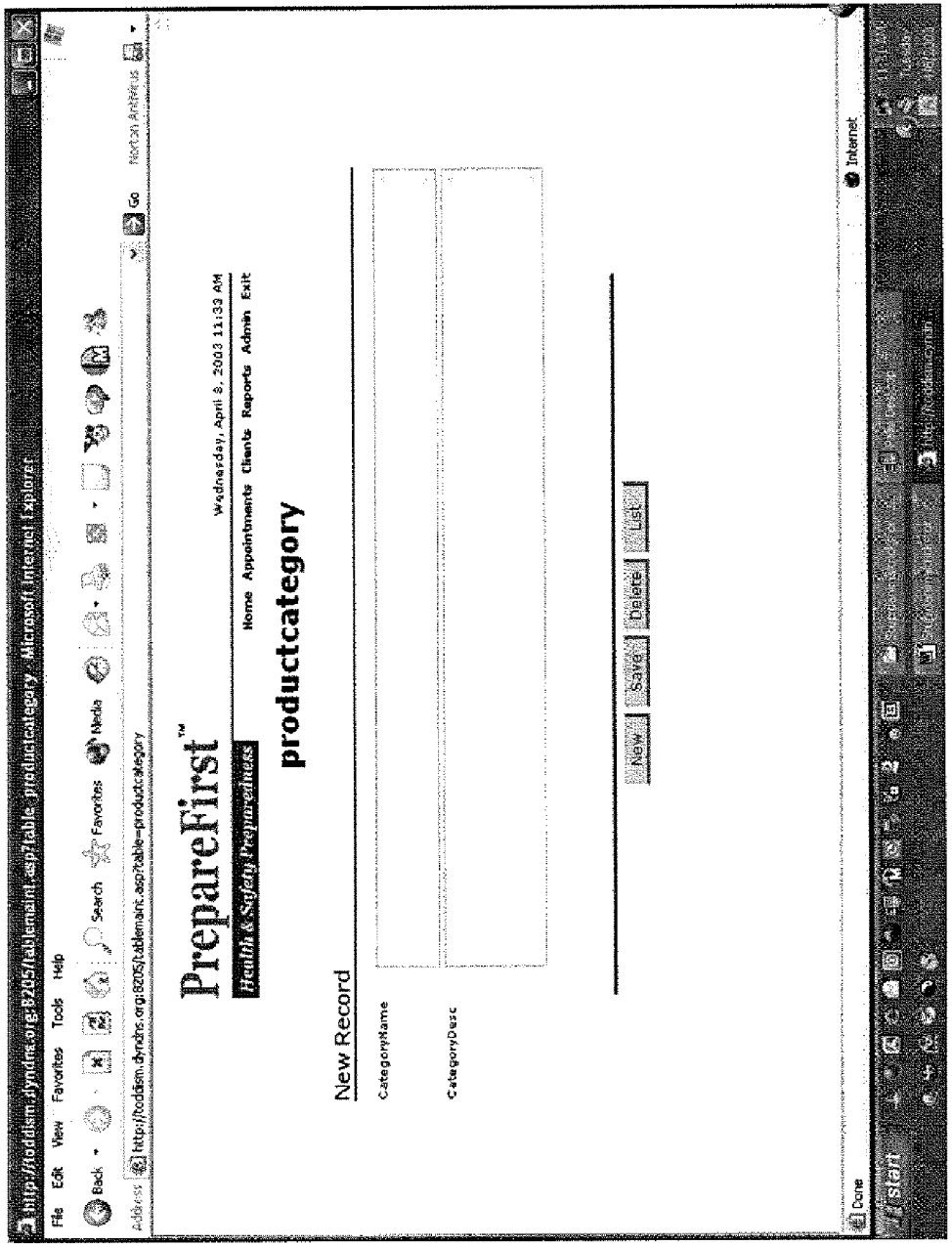

FIG. 35 shows a product category GUI, according to an illustrative example and exemplary embodiment of the present invention.

FIGS. 36 and 37 show questionnaire creation GUIs, according to illustrative examples and exemplary embodiments of the present invention.

Figure 38:
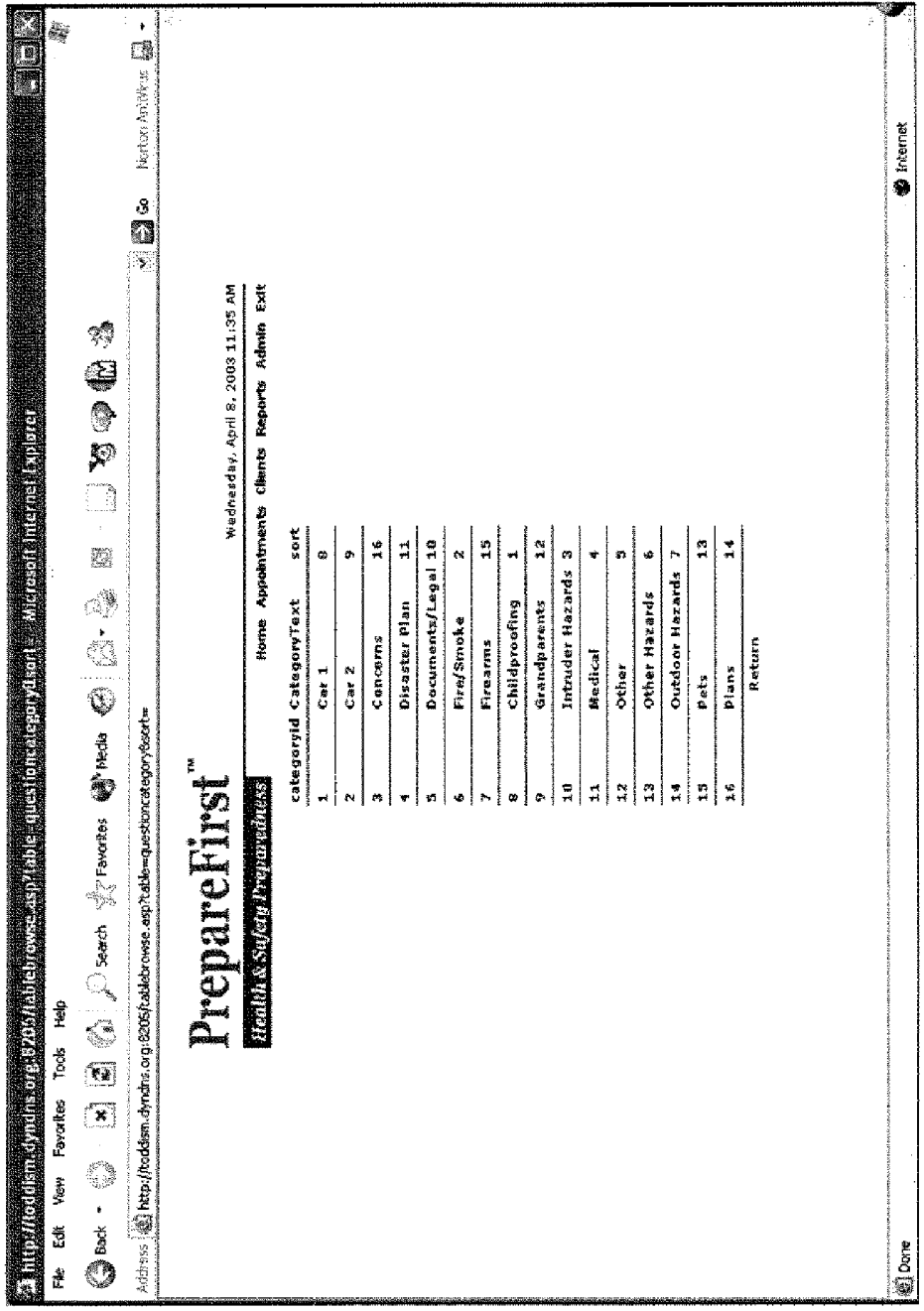

FIG. 38 shows a manage question category GUI, according to an illustrative example and exemplary embodiment of the present invention.

Figure 39:
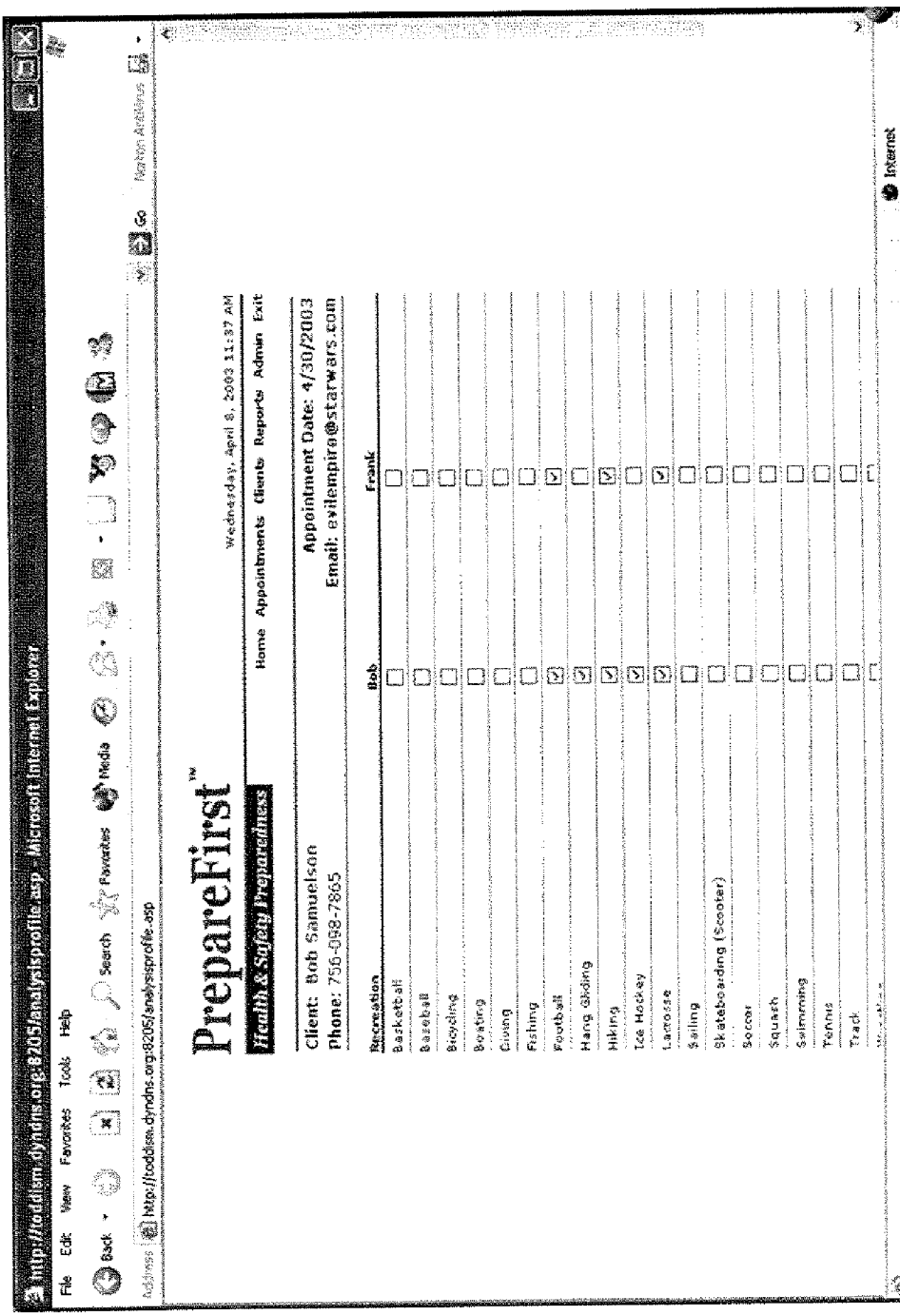

FIG. 39 shows a manage profile attributes GUI, according to an illustrative example and exemplary embodiment of the present invention.

Figure 40:
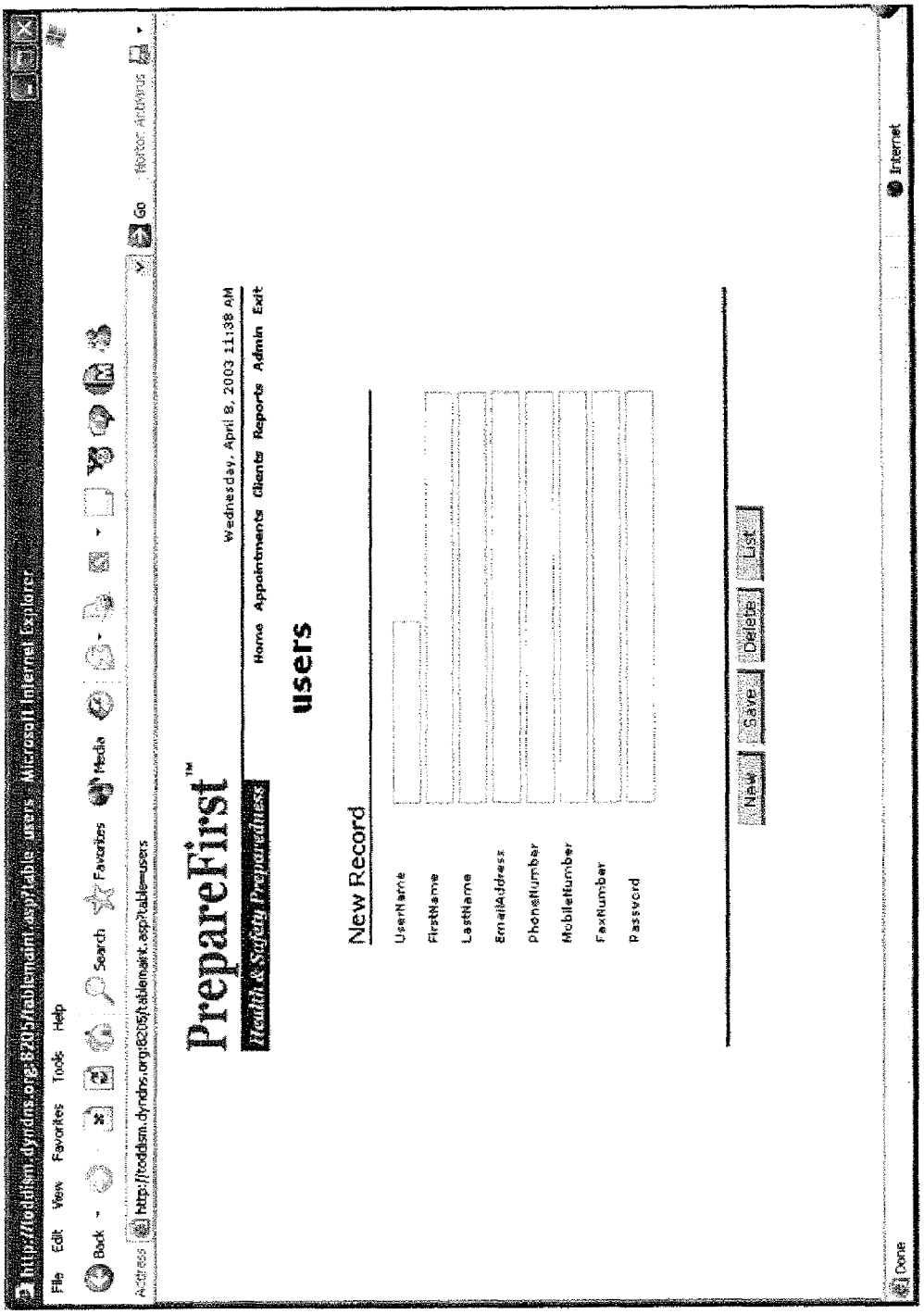

FIG. 40 shows a user rights hierarchy GUI, according to an illustrative example and exemplary embodiment of the present invention.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The present invention is described below with reference to block diagrams and flowchart illustrations of systems, methods, apparatuses and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto one or more general purpose computers, special purpose computers, or other programmable data processing apparatuses to produce a system of one or more machines, such that the instructions that execute on one or more computers or other programmable data processing apparatuses create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Referring now to FIG. 1, a Health, Safety & Security (HSS) hazards and solution identification system 100 in accordance with an illustrative embodiment of the present invention is shown. Generally, the HSS hazards and solution identification system 100 includes a HSS system 105 that receives input data from users 115 that use the HSS system 115 to gather on-site data as a result from conducting lifestyle based HSS consultations and analyses. The users 115, as explained in greater detail below, also input client-related data and may input company and/or transaction data, and/or product data into the HSS system 115. As referenced herein, clients are recipients of reports generated by the system 100 with the help of one or more users 115 or user-consultants. Users 115 may utilize a laptop computer, hand held computer, or the like to input information in the system 100. The users 115 input data may be received via one or more networks 122, such as the Internet such that the HSS system 105 represents an Internet-accessible system. Alternatively, as is shown by the dashed line between the user(s) 155 and the HSS system 105, users may access the system 105 directly, which may occur when the HSS system resides on a computer local to a user 115, such as a handheld computer.

As shown in FIG. 1, the HSS system 105 also includes resource(s) 120 that may be provided from one or more entities. Resources can include products, services, and information that may be identified by the HSS system 105 to mitigate or eliminate HSS risks. The resources can include the cost of products, services, and the like, expiration dates of such products, and other pertinent information related to HSS solutions, such as feature comparisons, price comparisons, and the like. Additionally, the resource(s) may include statistics, guidelines and practices that may be used by the HSS system 105 to identify the applicable resources based on the user-input data. It should be appreciated that some or all of the resource(s) may be input by a user 115 and/or administrator and/or stored within the HSS system 105; therefore, the resource(s) illustrated in FIG. 1 may be an optional element in the system. Additionally, as with the users 115 communication with the HSS system 105, the system 105 may retrieve or receive resource(s) via one or more Network(s) 122, such as the Internet, or may access or receive the resources 120 directly (as illustrated by the dashed line). The HSS system 105 may also communicate with a central office 116 operable to communicate with the one or more user(s) and the HSS system. According to one aspect of the invention, the central office 116 may serve an administrative function by acting as a central data repository and as an entity from which administrative control over the HSS system 105 is executed, as described in greater detail below.

The HSS system 105, and more particularly the HSS module 135 described in greater detail below, receives the user-input data and processes the data to generate a client-specific report that identifies hazards and recommended solutions, including but not limited to specific products, services, and information designed to mitigate or eliminate the impact of the identified hazards. The HSS module 135 also prepares a quote for suggested products, services and permits a user to schedule delivery of such to a client. Other functions of the HSS module 135 will be described in greater detail below with respect to the GUIs generated by the HSS module 135 for receiving and displaying information.

Although described with reference to FIG. 1 as communicating only with one or more generic resource(s) 120, which may represent a data entity or provider of resource(s), it should also be appreciated that the HSS system 105 may interface to one or more systems to receive or identify products, services and other items that may be provided to a client. The HSS system 105 may also communicate and/or permit user access to tools for gathering, recording and managing information pertaining to their own health, safety and security profile. Therefore, while a user 115 is described herein as a person that uses the system 105, and has particular rights as described below, a user may also represent a client for which the system 105 identifies hazards and recommends solutions. A user may also represent an administrator with authority to make changes to the rights of other users, change the functionality of the system 105, access confidential reports, and the like.

Communications with each of the entities and/or their respective systems in FIG. 1 may utilize the one or more networks 122 and/or may utilize one or more other networks (not illustrated), dedicated communication links, and/or direct data entry or receipt. Still other entities may provide data to the HSS system 105. It will also be appreciated that the methods of communicating with the HSS system 105 may include any method well known to those of ordinary skill in the art. Thus, the present invention is not limited to a system in which the HSS system 105 receives communications in a particular format or mode or via a particular operating system or via particular hardware. For instance, although the present invention can be implemented by utilizing the Internet to facilitate communications directly between a particular PMS 115 and the HSS system 105, any variety and/or combination of other communication methods can be used to interact with the HSS system 105. Moreover, although not described in detail herein, it will be appreciated that some or all communications in the system 100 shown in FIG. 1 may be secure to maintain the confidentiality of data and to authenticate users of the HSS hazards and solution identification system 100.

As shown in FIG. 1, the HSS system 105 includes at least one interface 150 to permit the HSS system to collect user-input data and resources from one or more users(s) 115 and/or resource(s) 120. The interface permits the HSS system 105 to receipt of data from users 115 and resources 120 employing different software, data formats, communication protocols, and the like. It will also be appreciated that although the receipt of user data is described herein as a manual process, the receipt of all data used by the HSS system 105, and more particularly, the HSS module, may be an automated process, such as may be performed by batch receipt of data.

The exemplary HSS system 105 of the HSS hazards and solution identification system 100 includes a processor 140, operating system 145, bus 160, and one or more storage devices 155 in addition to the interface(s) 150 and the afore-mentioned HSS module 135 residing within a memory 110. The bus 160 includes data and address bus lines to facilitate communication between the processor 140, operating system 145 and the other components within the HSS system 105, including the memory 110, the interface(s) 150 and the one or more storage devices 155. According to one aspect of the invention, the system 105 may represent a system of distributed components that are connected by the bus 106. The processor 140 executes the operating system 145, and together the processor 140 and operating system 145 are operable to execute functions implemented by the HSS system 105, including executing software applications stored in the memory 110, as is well known in the art. The memory 110 may include random access memory, read-only memory, a hard disk drive, a floppy disk drive, a CD-Rom drive, a DVD-Rom drive, optical disk drive, or the like, for storing information on various computer-readable media.

Specifically, to implement the methods described herein, the processor 140 and operating system 145, with the HSS module 135 and I/O interface(s) 150, receive commands and instructions and execute the functions described herein. Among other functions, these commands include configuration commands from a user-administrator 115. The commands permit the establishment and/or editing of user rights, system functionality, and the like as will be described below. The HSS module 135 also receives commands from users 115 of the system 105, which as described above may input data into the system 105. This data may include on-site data related to an analysis inspection (e.g., an analysis of the client's home or premises) or the like, as will be described below. This data may also include client data specific to a client, such as client characteristics (age, mobility, etc.), as will be described in detail below. The HSS module 135 utilizes user-input information and/or information related to a client stored in the one or more storage devices 155 to identify HSS hazards and to suggest products, services and information that may mitigate or eliminate such HSS hazards. The HSS module 135 is operable to produce reports for clients that summarize the products, services and information pertinent to the client, as detailed below.

The HSS module 135 is operable to store and retrieve data from the one or more storage devices 155, including on-site data 157, client data 160, product data 156, company & transaction data 158, and Statistics, Guideline and Practices (SGP) data 159. As described in detail below, the company and transaction data may include client-specific data and records accessible by an administrator of the system 105, for instance reports on payments, clients consulted, calendars for scheduling analyses and/or delivery of products, services or information, and the like. The SGP data 159 may be used by the HSS module 135 as rules to identify the applicability of certain products, services and information for a particular client, and/or may be displayed to a user (including a client) to illustrate how a client scores or ranks to permit the client to view their relative HSS preparedness.

The on-site data 157 and client 160 data, as described above, may store information received from a user as a result of a consultation and client-site analysis. Exemplary on-site 157 and client data 160 includes data used to populate the illustrative GUIs of FIGS. 3-40, described in detail below. The product data 156 includes data on products, services and information, including product descriptions, costs, comparisons, and the like. The product data 156 can also include any resource(s) 120 received by the HSS system 105.

Although the data sets described above are illustrated as separate within the one or more storage devices 155, it should be appreciated that the data may be stored within a single database or location. Therefore, while the data types described herein are useful to explain the type of data received, generated and published by the HSS system 105, the data may be stored together by the system 105 or in diverse tables and/or databases. Thus, it will be appreciated by one of ordinary skill in the art that the division of data has no impact on the operation of the HSS module 135 described herein. Therefore, the data fields, categories and tables described in detail herein represent only a representative division of data, where such items may be stored in any manner within the one or more storage devices 155.

The one or more storage devices 155 are connected to the bus 160 by an appropriate interface and can include random access memory, read-only memory, a hard disk drive, a floppy disk drive, a CD-Rom drive, DVD-Rom drive, optical disk drive, or the like, for storing information on various computer-readable media, such as a hard disk, a removable magnetic disk, or a CD-ROM disk. In general, the one or more storage devices 155 provide non-volatile storage to the HSS system 105.

The HSS module 135 is further operable to provide GUIs that permit users to input data into the system 105 and to view reports and results generated by the HSS module 135. The GUIs also provide administrators the ability to configure the system 105 to identify the content users can view and/or input depending on their authorization. According to one aspect of the invention, the GUIs provide questionnaires and other fillable forms via which the user can enter client 160 and on-site data 157, as will be described in detail below. The function and purpose of the GUIs provided by the HSS module 135 are described in more detail with respect to the illustrative GUIs described with respect to FIGS. 3-40.

It should be appreciated that although the HSS module 135 is described herein as software residing within the memory 110, the HSS module 135 may alternatively include a combination of software and hardware, or only hardware. Furthermore, although illustrated as located entirely within the HSS system 105, one or more of the HSS system 105 components can be distributed such that they are in whole or part external to the HSS system 105. As an illustrative example, the one or more storage devices 155 may in fact be external to the HSS system 105. Additionally, one or more of the data sets (or files) 156-160 within the one or more storage devices 155 may be located external to the HSS system 105 and accessed remotely.

Further, it should be also appreciated by one of ordinary skill in the art that one or more of the HSS system 105 components described with respect to FIG. 1 may include several components, which are either local to each other or which operate in conjunction with each other to permit the HSS module 135 to perform the processes described herein. One or more of the HSS system 105 components may also be combined and/or may be distributed on different computers, systems, platforms, and the like. Therefore, it should be appreciated that the illustrative system 100 shown in FIG. 1 is exemplary, and that almost any combination of software and/or hardware may be utilized to perform the functions described herein. The methods and processes implemented by the HSS system 105 and the HSS module 135 will next be described with reference to FIGS. 2-40.

FIG. 2 shows a high level block diagram flow chart illustrating a risk assessment and solution identification process performed in accordance with an illustrative embodiment of the present invention. First, using the HSS system 105 described above, safety information related to potential safety hazards existing at a client location is collected (block 200). This information can include on-site data, client-data and other user-input data. Next, the product and service information (including all information provided by the resource(s) 120) is collected relating to one or more products or services for mitigating potential safety hazards (block 205). Finally, the HSS system 105 and more particularly, the HSS module 135, automatically identifies, using the safety information, the one or more products or services (block 210).

Next, FIGS. 3-40 show illustrative GUIs generated to permit the input of information to identify HSS risks and to generate client reports as described in detail hereinafter. According to one aspect of the invention, the GUIs may be Internet-accessible. However, the GUIs may also be provided locally and accessed directly from a single computer. According to still another aspect of the invention, the GUIs may be stored locally and accessed remotely, such as in an Application Service Provider type model. It will be appreciated that the GUIs are illustrative only, and that many alternative GUIs may provide the functions described below with respect to FIGS. 3-40.

FIG. 3 shows a system and data security GUI 300, according to an illustrative example and exemplary embodiment of the present invention. According to one aspect of the invention, HSS system 105 and data security are maintained through a hierarchical method of administrating access and usage rights, effected through use of unique user names and passwords entered through the system and data security GUI 300 of FIG. 3. A user is assigned certain rights to access, view, modify, and/or make use of HSS system functionality and data by an administrator based on such user's functional role with the system 100. According to one aspect of the invention, passwords, once issued, may be altered by a user to meet his or her requirements. According to another aspect of the invention an administrator manages the permissions granted to each user and can effect the revocation or modification of such rights at any time. This process is described in greater detail in below with respect to FIG. 40.

The HSS module 135 is operable to discourage or prevent unauthorized use and/or dissemination of data by protecting various types of data. According to one aspect of the invention, general system data may be protected by locking out a user from the system 105 if the remote user's device (e.g., a computer from which access to the HSS system 105 is obtained) has not received a new "key" within a certain predetermined timeframe and/or a request for a new "key" is received from an unexpected device ID. It will be appreciated by one of ordinary skill in the art that well known encryption techniques may therefore be used to protect unauthorized access to system 100 data. According to another aspect of the invention, the system 100 provides a mechanism to identify potential fraud committed by a user by tracking the creation and deletion of data in the storage device(s) 155 from all users 115. Creation and deletion records, which may be stored within the company & transaction data 158, which may then be available to an administrator to identify is a further inquiry is required.

FIG. 4 shows an appointment GUI 400, according to an illustrative example and exemplary embodiment of the present invention. The appointment GUI 400, which may be accessed via selection of a button near the top of the screen, may be used by a user to manage and establish appointments with clients. According to one aspect of the invention, a client or potential client's data that is collected includes the client name and contact information, which will include a zip code or the like. Based on this information, the HSS module 135 may compare the client address to zip codes or other geographic criteria associated with a particular consultant associated with the system 100 in order to assign each consultant clients.

According to one aspect of the invention, leads are managed in order to ensure that each respective/appropriate user communicates with his or her prospective clients in a timely manner to schedule appointments and render services. When a lead is entered into a consultant's queue, the date and time is recorded as well as the date and time the central office captured the lead. A consultant, after communicating with the prospective client, either marks the lead as closed or creates a client record directly from the lead record. The structure of the lead record is similar to a [HouseholdMember] record, which allows the system 100 to automatically establish the "Primary Member" for the newly created client record. After login, the queue is displayed as well as the length of time since the lead was received. Leads may be color coded to indicate the amount of time that has passed since the consultant's receipt of said leads. When the consultant performs an update/synchronization procedure between his or her device and the central office, lead queue status is automatically transmitted. Email alerts may be sent automatically by the system 100 to designated central office (management) personnel when a predetermined amount of time has passed and satisfactory action has not been taken with regard to a given lead. The system 100 also provides a variety of reports, including but not limited to lead status by consultant, Zip Code, or Region.

The calendar lists all scheduled appointments for the specific user on his or her respective calendar days. The appointment times are hypertext "hotlinks" to the relevant details of each such appointment. A "mouse-over" of the listed appointments displays the respective client's name and primary contact information (e.g. phone number). Each day of the calendar also provides a hotlink to add a new appointment to the user's schedule for that day. The user navigates through the calendar via a variety of controls designed to permit efficient movement to the specific timeframe of interest to the user (e.g. "month view", "week view", "day view", "change year", "change month", "advance", "go back", "go to today", etc.).

FIG. 5 shows a client list GUI 500, according to an illustrative example and exemplary embodiment of the present invention. As illustrated, the client list GUI 500 may present a user (such as a consultant) with a queue which the user works through to contact and qualify prospective clients, arrange appointments, and establish a client service agenda which the user will implement on behalf of the Company. The system 100 also provides a mechanism to assist a user in determining the exact location of a client appointment so as to ensure effective time management and travel efficiency. This is accomplished through various means including the capture of a "closest major intersection" at the time the initial client contact is made, the importing of data from Mapquest® (or a similar service provider), and the use of travel distance data. The system 100 also provides a mechanism for the association of a client lead with a predetermined territory in order to assist in making appropriate assignments to downstream users.

FIG. 6 shows an appointment setup GUI 600, according to an illustrative example and exemplary embodiment of the present invention. According to one aspect of the invention, the appointment setup GUI 600 permits a user to view and manipulate appointment details. To schedule an appointment, a user may choose a client name from a drop down list of clients known already to the system, including but not limited to new leads, or the user may click "New" to enter a new customer into the system 100 through an interface designed therefor. Once a client has been identified, the user indicates the date, time, and duration of the appointment, as aided by a list displayed of pre-existing appointments and which highlights "Available" time in between appointments of estimated duration. Pre-existing appointment times in the list are hot-linked in a manner which causes the associated data to be loaded into the top of the form so the user may edit/modify the pre-existing appointment details. Likewise, the client names are hot-linked to an interface which permits editing/modification of client contact data. The user also specifies whether the appointment is being set in order to implement a previously established client service agenda or whether a new client service agenda is to be created. The user may save the new appointment and/or return to the initial appointment GUI 400 of FIG. 4 as necessary. The system 100 checks to ensure the user does not exit the appointment scheduling interface accidentally without saving a desired appointment.

FIG. 7 shows a client service agenda GUI 700, according to an illustrative example and exemplary embodiment of the present invention. According to one aspect of the invention, the system 100 provides a mechanism for defining a client service agenda that specifies the order and nature of services to be rendered by a user to a client. The client service agenda GUI 700 permits a user (such as a consultant) to step through a specified work flow structure to ensure all aspects of a client service appointment are conducted and recorded correctly. The data fields provided by the client service agenda GUI 700 include, but are not limited to, the following: <jobid>, <customerid>, <createdate>, <updatedate>, <active>, <analysisstatus>, <clientstatus>, <discussionstatus>, <profilestatus>, <quotestatus>, <inspectionstatus>, <reportstatus> and <orderstatus>. At the time an appointment is established by a user, the user must specify whether the purpose of the appointment is to effect the completion of a pre-established client service agenda; if not, the user can create a new client service agenda. As shown by the client service agenda GUI 700, this is done by selecting the appropriate item from the choices (including but not limited to choices comprising a full range of services or a limited range such as training only, consultation only, etc.) presented to the user at the time the user identifies the client with whom the appointment is being made. The user must "sign off on" (affirm the completion of) each step in the process by selecting a status value. Status values can be null (not set), "N/A" (not applicable) or "Complete."

According to one embodiment of the invention, A client service agenda is made up of multiple tables which may include, but are not limited to, the following:

[Analysis]—an instance of an Analysis.

[Analysis Locations]—an Area (or floor, or general location)

[Analysis Sublocation]—a defined space or room inside an Area (or general location).

[Analysis Sublocation Hazard]—Hazards that must be evaluated for an [Analysis Sublocation].

[Consultation]—an instance of both an Analysis Q & A and a Consultation.

[Consultation Answers]—the answers selected by a consultant when performing an Analysis Q & A and Consultation.

[Analysis Quote]—the data behind the Analysis price estimate. Includes, but is not limited to, square feet and cost for increments of space that are to be inspected.

[Analysis Quote Details]—one record exists for each level in a structure. The width, depth and percent usage are stored and totaled in the related [Analysis Quote] record.

[Analysis QuoteServices]—one record exists for each additional activity or service that may be included in the quote.

[Analysis Hazard Solution]—the products and services that could be used to correct or mitigate the effect of a defined risk or combination of hazard and hazard status. Includes the number of hazards in the sublocation as well as the number of products recommended. This is used to create the client report.

[Analysis Product]—the principal data included in the client report which is generated from [AnalysisHazardSolution].

[client Order]—the metadata header record containing the relevant client order data.

[client Order Solution]—the Solutions and quantities selected by client during the client Order review process.

According to one aspect of the invention, when a user clicks the time hotlink in the appointment calendar to "open" a given appointment for a given client, the user is presented with the client service agenda which was selected at the time of appointment setup. If the client service agenda is not the correct one, the user may select an alternative. Otherwise, the client service agenda GUI 700 prompts the user to step through the listed tasks.

Each section of the client service agenda GUI 700 provides high level details about the status of the work being (or to be) performed for a given client. According to one aspect of the invention, the details available within each section of the client service agenda GUI 700 may be expanded and viewed by checking the "view" checkbox next to the respective client service agenda item. FIG. 8 shows a second view of a client service agenda GUI 800, according to an illustrative example and exemplary embodiment of the present invention after the "view" checkbox is selected. A user may also view all details at once by clicking the hotlinked "View" column title; clicking a second time suppresses all details. A user makes an appropriate selection from the "Status" drop down box in each section to indicate that a given task is "Complete" or "N/A (not applicable)." The system 100 provides background validation that each such task has in fact been completed if it is being reported as such. The system 100 may also be modified to automatically identify certain tasks as complete based upon review of the data gathered in connection with such tasks.

Each of the tasks listed in the client service agenda GUI 700 constitute hotlinks to the associated functionality which a user employs to complete the relevant task. A user clicks the task hotlink, is taken to the area where the work is completed, then exits that area and is returned to the client service agenda GUI 700. Only by a user's completion of all items is the client service agenda deemed complete and finalized by the system 100. Additionally, only by completing certain tasks in the list can certain other listed activities be enabled, such as the fact that an analysis must always be completed prior to a user being able to print a client report for delivery to a client.

The sections of a client service agenda GUI 700 can include "contact info", "consultation", "analysis quote", "analysis profile", "analysis Q&A", "analysis inspection", "analysis payment", "kit configuration", "notification", "education", client report", "client order", and "confirm order". A summary of each is shown in table 1, below:

TABLE 1

| Client Service Agenda GUI sections | |
|---|---|
| Contact Info | provides a quick summary of the status of, and access to, the respective client's address, phone and email data, associated persons, and other relevant information. |
| Consultation | provides a high level summary of the extent to which a Consultation has been completed for a client, and access to said Consultation. |
| Analysis Quote | provides a summary of, and access to the mechanism for estimating, the service fee to be charged to a client in the event said client elects to purchase an Analysis, as well as a mechanism for a client to agree to the terms of said Quote. |
| Analysis Profile | provides a high level summary of the extent to which a Profile has been completed for the given members of a client Group during the course of an Analysis, and access to said Profile. |
| Analysis Q&A | provides a high level summary of the extent to which the Question and Answer section has been completed during the course of an Analysis, and access to said Analysis Q&A. |
| Analysis Inspection | provides a high level summary of the extent to which a physical premises and/or vehicle inspection and testing has been completed during the course of an Analysis, and access to said Analysis Inspection. |
| Analysis Payment | provides a summary of, and access to the mechanism for recording, a client's payment for an Analysis, including a (re-)acknowledgement of the associated terms of sale. |
| Kit Configuration | provides the status of the extent to which the system 100 has utilized data collected from or about the client to configure and customize the contents of one or more kits designed to provide increased client health, safety and/or security preparedness, and access to Kit Configuration functionality. |
| Notification | provides a report of the nature of the items which the system 100 has identified will be tracked and reported to a client on a regular basis to promote ongoing health, safety and security preparedness, and access to said Notification functionality. |
| Education | provides status information as well as access to the mechanism for a consultant to identify, quote, confirm, and conduct health, safety and/or security-related education for a client. |
| Client Report | provides a high level summary of, and access to, the client report resulting from the items that have been analyzed and tested, and data that has been gathered, during the course of an Analysis. The client report may only be printed once the user has confirmed that all required precedent activities have occurred |
| Client Order | provides status information as well as access to the mechanism for a client to review (with or without the assistance of a consultant) the Solutions |

TABLE 1-continued

| Client Service Agenda GUI sections | |
|---|---|
| | recommended for purchase in the client report, with the objective of the client's determining the final assortment of Solutions that client will purchase from the Company as affirmed via the confirm order process. |
| Confirm Order | provides status and the mechanism for a client (with or without the assistance of a consultant) to: i) confirm said client's decision to purchase the solutions contained in the finalized client order, and ii) effect and/or record the event of payment. |

Once all component elements of a client service agenda have been completed and the client service agenda is saved, a "CSA Completed" status indicator appears at the bottom of the client service agenda GUI 700, indicating satisfaction of all items.

It will be appreciated that the selection of "Contact Info" from the client service agenda GUI 700, 800 shown will result in the presentation of a client service contact GUI 900, as is shown in FIG. 9, according to an illustrative example and exemplary embodiment of the present invention. Certain basic information must be entered into the system 100 for any prospective client for whom an appointment (and a client service agenda) will be established. The system 100 validates that certain required fields have been filled out at the time a user enters the client's name as a prospect.

A user's selection of the "clients" tab at the top of the main menu generates a list of all clients authorized for viewing by the respective user. In the case of a field consultant, the list will display all clients that are 1) leads and 2) current or past appointments of a user. An exemplary embodiment of a client list GUI 1000 is shown in the illustrative example of FIG. 10. The client list GUI 1000 permits a user to sort clients according to data contained in the displayed columns by clicking the header of each column. The GUI 1000 is designed to provide a quick reference to the principal data for each client to avoid having to drill down deeper for routine contact or descriptive information. The client list GUI 1000 contains a reference to each person associated with the primary client whose information is important to collect to the extent it will impact the results of the analysis and recommendations made by the system 100 regarding the client's situation and needs. If more information is needed or an individual client contact record requires updating, the client names constitute hotlinks to the underlying full data record for each client as depicted in FIG. 9, described above.

It will be appreciated that each client contact record contains a variety of pertinent data about the relevant client, including but not limited to address, contact information, company name, title, and dependents. An individual person's data within a client contact record is considered a subrecord, and each such person is referred to as a client group member. This information may be stored as client data 160. Switches located within each display of a subrecord permit the user to enable or suppress the full display of data which may or may not be desirable based upon the amount of data needed by the user, the need to modify data, and/or the user's PC monitor size constraints.

FIG. 11 shows a client record GUI 1100, according to an illustrative example and exemplary embodiment of the present invention. This GUI 1100 references associated links within the database, also contains a summary of all activity pertaining to a client, including but not limited to appointments, profile(s), communications, client service agenda, client orders, and the like.

FIG. 12 shows a consultation GUI 1200, according to an illustrative example and exemplary embodiment of the present invention. The consultation GUI 1200 appears when a user chooses 'Consultation'. from the consultation section of the client service agenda GUI 700, 800. The consultation GUI 1200 provided by the HSS module 135 displays a list of consultation questions which the user poses to the client and records the client's answers thereto. All questions may require objective answers selectable from available choices, but which may be appended by ad hoc notes added by the user based upon the user's knowledge or client's request. The use of predetermined choices is designed to maximize the structure, efficiency, and accuracy of determining the recommendations which will be made by the HSS module 135 to the client based on the data collected. User judgment and experience may be brought to bear in any context where incremental data gathering, editorial, and/or recommendations are deemed appropriate; however, the system 100 design attempts to minimize the need for subjective user input. Consultation questions are grouped into logical categories comprising the major topic areas that are the focus of the respective client service agenda. The client's responses to the consultation questions are stored and combined with other data (including but not limited to physical inspection data, product data, client profile attribute data, analysis Q&A data, expiration tracking data, etc.) in order to compile the client's overall lifestyle-based health, safety and security profile from which the client report is generated by the HSS module 135.

During a consultation, the system 100 collects information including, but not limited to, a client's health, safety, and security-related issues, concerns, history, and risks. This data is stored in the client data 160 and/or on-site data 157 and linked to the client service agenda, which contains additional information regarding, but not limited to, a client's physical structures, vehicles, and household/group members. Each identified risk, hazard and hazard status combination, health statistic, activity, concern or other attribute may be pre-linked to one or more product, service, resource, web site (URL), kit, or other product, service, resource, or other solution through the solution object, which may be stored within the SGP data 159. A user may also associate products and services to a client ad hoc during any phase of a consultation, which will be received by the HSS module 135 and added to the client report. Each link record contains the username of the user that performed the consultation, the ID of the computer used, and the client ID. In this manner, the system 100 may track individual productivity.

According to one aspect of the invention, the consultation record, which may be stored as company and transaction data 158, also contains the beginning and end time for the process. The consultation phase begins when the system 100 pulls questions and their respective answers from the [question] and [answer] tables. The first time the consultation page is displayed, the system 100 records the start time. The system 100 checks the table [Consultation Answers] for existing client answers and displays them on the screen. Every question must be answered or indicated as not applicable in order for this component of the client service agenda to be deemed complete. Among other data, the table [Job] contains the status of this portion of the client service agenda.

Although not illustrated in the consultation GUI 1200 of FIG. 12, at the bottom of the consultation GUI 1200 is a "free form" text area available for a user to input and/or highlight information that is urgent or that the user otherwise believes should be captured. This text is saved in the consultation record and is subsequently displayed on the client report. During a consultation, the system 100 indicates to a user that a particular answer constitutes an urgent situation based upon the data record of the respective question and answer. If, during the course of a consultation, a user determines on his or her own that a given answer is urgent regardless of the system's default recommendation, a checkbox is available which, when checked, indicates that the user has determined that the situation requires urgent attention. This is displayed in the client report. After the data is saved in the table [Consultation Answers], the HSS module 135 checks the number of consultation questions against the number of answers. When there is an answer for each question, the consultation phase is indicated on screen as complete, and the time of completion is noted by the HSS module 135 and stored in the company and transaction data 158.

Next, FIG. 13 shows an analysis quote GUI 1300, according to an illustrative example and exemplary embodiment of the present invention. According to one aspect of the invention, the HSS module 135 provides a mechanism for estimating the service fee to be charged to a client in the event a client elects to purchase an analysis generated by the HSS module 135. By selecting 'analysis quote' from the client service agenda GUI 700, 800, the user is presented an interface where square footage, activities, services, and other data may be entered, combined with pricing data, and the resultant fee displayed. The analysis quote may represent a basic initial form of client order that the client agrees to in order to initiate an analysis or another service to be rendered through a client service agenda (the specific activities to be completed by the user, or user-consultant). Payment is made by the client (via the analysis payment process described hereinafter) at the time the respective service is rendered.

The HSS module 135 also establishes attributes and associates them with each member of a client group in order to permit the present invention to generate recommendations of HSS-related products and other solutions pertaining to such attributes that a client may wish to consider for purchase or implementation. Attributes are data elements comprising unique items (including, but not limited to, recreational activities, work-related activities, travel activities, risk factors, medical history, medications being taken, other characteristics, etc.) which, by their association with a client group member, contribute to the HSS Module's 135 overall assessment and recommendation concerning said client group member's health, safety and security risk profile. According to one aspect of the invention, the attributes are stored as SGP data 159 and/or as client data 160.

Analysis profile data is made up of at least two different types of data. The first is attributes listed in the [Attribute] table which includes a list of activities, characteristics, risks, etc. which may pertain to a client group member and which are gathered in a binary ("yes" or "no") manner. During the analysis profile section of a client service agenda GUI 700, 800, these attributes are listed in a grid. Each client group member is listed at the top of the user interface across the X axis, and the individual attributes are listed down the Y axis. Each cell (the intersection of a client group member and an attribute) includes a checkbox. Checking any given box indicates the respective attribute is applicable to the respective client group member. The resulting association is saved in the [Member Attribute] table.

An [Attribute] record may have a "describe" flag set. If it is true (or not zero) the system 100 includes a text area where a user may type in an attribute not previously included in the system. In addition to simple binary attributes, there are some potential characteristics of a client group member with regard to which the selection of an answer more involved than a binary "yes" or "no" is desirable from a large(r) list of possible choices. Examples would be: historical medical attributes, specific allergies, medications being taken, vehicle types driven, etc. For these types of characteristics, the table [Profile List] is used to name each respective list. FIG. 14 shows an illustrative attribute association GUI 1400, according to an exemplary embodiment of the present invention. The name of the given characteristic is displayed along the Y axis. In each cell (the intersection of a client group member and characteristic list name) in the row, a drop down selection contains the possible values. Selection values are stored in the table [ProfileListValue]. More than one selection can be made by using the "Control" (<<CTL>>) key if more than one answer is appropriate. The selections are stored in the [MemberProfileList] table. Each [Attribute] or [ProfileListValue] record may be associated to one or more [Solutions] record. The [Solutions] table contains: the ID of the [Attribute] record or [ProfileListValue] record, a code to indicate the type of link, and a link to one or more product, kit, service or other solution. The client report aggregates all of the data input using the analysis profile, analysis inspection, analysis Q&A, and consultation GUIs, and online self-service client survey, and establishes the proposed, associated client order.

According to one aspect of the invention, at the bottom of the attribute association GUI 1400 is a "free form" text area available for a user to input and/or highlight information that is urgent or that the user otherwise believes should be captured. This text is saved in the [Analysis] record stored within the company and transaction data 158 and is subsequently displayed on the client report. During an analysis profile, the HSS Module 135 indicates to a user that a particular "answer" constitutes an urgent situation based upon the data record of the respective attribute. If, during the course of an analysis profile, a user determines on his or her own that a given attribute is urgent regardless of the system's 105 default recommendation, a checkbox is available which, when checked, indicates that the user has determined that the situation requires the client's urgent attention. This is displayed in the client report.

During an analysis profile, the HSS module 135 collects information including, but not limited to, a client's health, safety, and security-related issues, concerns, history, and risks. This data is stored within the one or more storage devices 155 and is linked to the client service agenda, which contains additional information regarding, but not limited to, a client's physical structures, vehicles, and household/group members. Each identified risk, hazard (i.e., a health, safety or security-related source of risk) and hazard status (i.e., the condition of a hazard) combination, health statistic, activity, concern or other attribute may be pre-linked to one or more product, service, resource, web site (URL), kit, or other solution through the solution object, as discussed herein. A user may also associate solutions (products, services, etc.) to a client ad hoc during any phase of an analysis profile. Each link record contains the username of the user who performed the analysis profile, the ID of the computer used, and the client ID. In this manner, the system 100 may track individual productivity.

The table [AnalysisProfile] provides a mechanism for data collected during an analysis profile to be isolated to a particular client service agenda, enabling multiple potential instances of client group member Profiles to be created over time. Each [AnalysisProfile] record contains, among other data, the beginning and end time for the process. The analysis profile phase begins when the system 100 first displays the associated grid for a client. The first time the analysis profile page is displayed and the first value is captured, the system 100 records the start time. The system checks the table [MemberAttribute] for existing client "answers" and displays them on the screen. Not every item must be "answered" in order for this component of the client service agenda to be deemed complete; completion is deemed to have occurred when "Profile Complete" is selected by the user. The data fields associated with the analysis profile section include but are not limited to: <profilelistname>, <profilelistid>, <profilelistvalue>, <profilelistvalueid>, <recreationid>, <recreationname>, <details>, <Householdmemberid>, <customerid>, <activityid>, <activitydesc>, <valuedesc> and <value>.

FIG. 15 shows an analysis question and answer GUI 1500, according to an illustrative example and exemplary embodiment of the present invention. The analysis question and answer GUI 1500 displays a list of questions which the user poses to the client and records the client's answers thereto. According to one aspect of the invention, the analysis question and answer GUI 1500 is selected by a user from the selection of 'Analysis Q&A' from the client service agenda GUI 700, 800. All questions may require objective answers which must be selected from available choices, but which may be appended by ad hoc notes added by the user based upon the user's knowledge or client's request. The use of predetermined choices is designed to maximize the structure, efficiency, and accuracy of determining the recommendations which will be made by the HSS module 135 to the client based on the data collected. User judgment and experience may be brought to bear in any context where incremental data gathering, editorial, and/or recommendations are deemed appropriate; however, the HSS module 135 may be implemented without the need for subjective user input. According to one aspect of the invention, analysis Q&A questions are grouped into logical categories comprising the major topic areas that are the focus of the respective client service agenda. The client's responses to the analysis Q&A questions are stored and combined with other data (including but not limited to physical inspection data, consultation data, client profile attribute data, product data, expiration tracking data, etc.) in order to compile the client's overall lifestyle-based health, safety and security profile from which the client report is generated by the HSS module 135 and presented to the client by the user.

During an analysis Q&A, the HSS module 135 collects information including, but not limited to, a client's health, safety, and security-related issues, concerns, history, and risks. This data is stored and linked to the client service agenda, which contains additional information regarding, but not limited to, a client's physical structures, vehicles, and household/group members. Each identified risk, hazard and hazard status combination, health statistic, activity, concern or other attribute may be pre-linked to one or more product, service, resource, web site (URL), kit, or other solution through the solution object. A user may also associate products and services to a client ad hoc during any phase of an analysis Q&A. Each link record contains the username of the user who performed the analysis Q&A, the ID of the computer used, and the client ID. In this manner, the system 100 may track individual productivity.

According to one aspect of the invention, the consultation record contains the beginning and end time for the Analysis Q&A. The analysis Q&A phase begins when the HSS module 135 pulls questions and their respective answers from the Question and Answer tables within the one or more storage devices 155, such as within the company and transaction data 158. The first time the analysis question and answer GUI 1500 is displayed, the HSS module 135 records the start time. The HSS module 135 checks the table [ConsultationAnswers] for existing client answers and displays them on the screen. Every question should be answered or indicated as not applicable in order for this component of the client service agenda to be deemed complete. Among other data, the table [ConsultationAnswers] contains the status of the analysis Q&A portion of the client service agenda.

It will be appreciated that at the bottom of the Analysis Q&A interface is a "free form" text area available for a user to input and/or highlight information that is urgent or that the user otherwise believes should be captured. This text is saved in the consultation record and is subsequently displayed on the client report. During an analysis Q&A, the HSS module 135 indicates to a user that a particular answer constitutes an urgent situation based upon the data record of the respective question and answer. If, during the course of an analysis Q&A, a user determines on his or her own that a given answer is urgent regardless of the system's default recommendation, a checkbox is available which, when checked, indicates that the user has determined that the situation requires the client's urgent attention. This is displayed in the client report. After the data is saved in the table [ConsultationAnswers], the HSS module 135 checks the number of analysis Q&A questions against the number of answers. When there is an answer for each question, the analysis Q&A phase is indicated on screen as complete, and once completion has been confirmed, the time of completion is stored by the HSS module 135.

Next, if a user chooses analysis inspection from the client service agenda GUI 700, 800, the HSS module 135 displays a sequence of GUIs 1600, 1700, 1800, 1900 of FIGS. 16-19 that permit, respectfully, 1) identification of the property in question; 2) selection of a general area to be analyzed (e.g. 3rd Floor, 2nd Floor, basement, outdoor, etc.); 3) selection of a relevant sublocation (e.g. bedroom, bathroom, roof, closet, staircase, etc.); and 4) access to the combination of a drop down box and a data entry field wherein the user may note any distinguishing feature(s) of the sublocation in order to permit easy and unique identification thereof within a report of multiple sublocations of a similar type. Identifying features are saved in an analysis record, which may be stored within the on-site data 157 of the one or more storage devices 155. Among other data, the analysis record contains the status of its portion of the client service agenda. For managerial and other purposes, the HSS module 135 records the order that areas and sublocations were added during the analysis inspection.

Sublocations are identified as belonging to the "indoor" or "outdoor" category at the time they are created as described hereinafter. According to one aspect of the invention, they can be presented to a user in alphabetical order. Likewise, once a user has "added" a new sublocation during the course of an analysis inspection, the hazards are listed in alphabetical order, with similar hazard-hazard status groups presented together. Regarding the list of sublocations inspected, however, the list may be presented in the order in which the sublocations were added by the user.

When a user enters the analysis data collection GUIs for a particular area and sublocation, as is shown in an analysis inspection GUI 2000 like that shown in FIG. 20, according to an illustrative example and exemplary embodiment of the present invention, a list of potential hazards and hazard statuses is displayed which prompt a user to enter all occurrences of such items which the user can locate within the sublocation. Typically, a user enters hazard occurrence data via drop down lists which "force" the recording of objective quantities selected from available choices, but which may be appended by ad hoc notes added by the user based upon the user's knowledge and judgment. The use of predetermined choices is designed to maximize the structure and efficiency of determining the recommendations which will be made to the client based on the data collected as well as to minimize the need for subjective user input. However, user judgment and experience may be brought to bear in any context where incremental data gathering, editorial, and/or recommendations are deemed appropriate. The HSS module 135 is designed to present hazards to a user in logical groupings and order so that a user may locate items quickly. During an analysis inspection, among other activities, a user may perform various tests, such as: water quality, radon, mold, air quality, etc. The HSS module 135 provides a user the ability to "flag" individual items in such a way as to identify them for subsequent focused follow up with a client (i.e. a question needing to be asked/answered, and/or an item requiring particularly urgent attention from the client to eliminate or mitigate a significant risk).

An authorized user may define hazards and hazard statuses as discussed in greater detail below. Hazards are stored in the hazards table, which may exist within the on-site data 157 or within an alternative location within the one or more storage devices 155. Similarly, hazard statuses are stored in the HazardStatus table. Each combination of a hazard and hazard status may have one or more solutions (products, services, and the like to mitigate or eliminate health safety risks) as assigned via the solution object. From the hazard maintenance page, a user chooses to associate one or more hazard statuses to a hazard. A page is displayed listing available hazard statuses on the left side of the page and hazard statuses already associated to this hazard on the right side of the page. A check box is located in front of each hazard status. By checking the boxes on the "available" hazard statuses and then choosing "Add >>", the selected hazard statuses will be associated to the hazard.

To remove a selected hazard status, the check box next to the selected hazard status is checked, and "<<Remove" is selected. Next to each selected hazard status is an additional checkbox. If the hazard—hazard status combination constitutes a situation that objectively should require urgent attention and that should be highlighted as urgent by default in the context of a client report, this is checked. To make a new hazard-hazard status combination urgent, the user checks the urgent check box next to the selected hazard status and clicks "Save Urgency Status." The table [HazardStatusLink] contains the association of hazards and hazard statuses as well as the urgency "flag." During an analysis inspection, the system 100 indicates to a user that a particular hazard—hazard status combination is urgent. If, during the course of an analysis inspection, a user determines on his or her own that a given hazard—hazard status combination is urgent regardless of the system's default recommendation, a checkbox is available which, when checked, indicates that the user has determined that the relevant hazard-hazard status combination requires the client's urgent attention. This is displayed in the client report.

During an analysis inspection, the system 100 collects information including, but not limited to, a client's health, safety, and security-related issues and risks. This data is stored and linked to the respective client service agenda, which contains additional information regarding, but not limited to, a client's physical structures, vehicles, and household/group members (client group members). Each identified risk, hazard and hazard status combination, health statistic, activity, test result, concern or other attribute may be pre-linked to one or more product, service, resource, web site (URL), kit, or other solution through the solution object, as defined. A user may also associate products and services to a client ad hoc during any phase of an analysis inspection. Each link record contains the username of the user who performed the analysis inspection, the ID of the computer used, and the client ID. In this manner, the system 100 may track individual productivity.

Among other data, an [Analysis] record contains the beginning and end time for the process. The analysis inspection phase begins when a user "adds" the first area and sublocation. The first time a sublocation is added, the system 100 records the start time. The system 100 checks the table [Analysis] for existing hazards inspected and displays them on the screen. Every hazard must be "answered" or indicated as not applicable in order for the analysis inspection section of the client service agenda to be deemed complete. After the data is saved in the table [AnalysisSublocationHazard], the system 100 checks the number of hazard—hazard status combinations completed vs. the potential number. When all potential hazard—hazard status combinations have been completed, the analysis inspection phase is indicated as complete, and the time of completion is noted in the system. As a section is completed, it is stored in the [Job] table. The table [Analysis] contains the status of its portion of the client service agenda. At the bottom of the analysis inspection GUI 2000 is a "free form" text area available for a user to input and/or highlight information that is urgent or that the user otherwise believes should be captured. This text is saved in the [Analysis] record and is subsequently displayed in the client report.

It should be appreciated by one of ordinary skill in the art that an analysis may be split and conducted by one or several users ("associate users") whose data is transmitted, assembled, and aggregated by one user ("lead user"). Once each user has completed his or her component element of the client service agenda, each such user may transmit his or her respective data collected to the data collection device of the lead user, whose device combines all data into the compilation that constitutes the definitive version of the client service agenda data. Once the system 100 has confirmed the successful aggregation of all partie's data and effected a successful backup thereof, the data collected by the associate users is removed from their data collection devices. The system 100 records the identifying code of the user who collected the data contained in the aggregation in order to provide an audit trail. Each associate user device each contains all of the relevant system 100 code. A [client] record is transmitted to each associate user's device so that the associate user is able to perform a component of the relevant analysis inspection. As each associate user adds areas and sublocations, the associated identifiers contain the concatenation of <LaptopID>, <userName>, <clientID> and an integer reflecting the order in which they were created. When the process is complete, an associate user can connect to the lead user device via wireless networking and transmits the completed data via secure sockets where the <username>, <LaptopID> and order are preserved. The data is then aggregated in the client report produced by the lead user.

Each data collection device contains sufficient storage area to permit each user to serve as an "account representative" with primary responsibility for communication with, and the satisfaction of, all clients assigned to the user. Through the routine updating procedure backup copies of all data located on the devices in the possession of each user in the field may be retained; however, each user remains largely self-sufficient (with certain specific exceptions) with regard to data collected by, or assigned to, said user which may be needed on an ongoing basis to answer a given client's questions or to address client needs which may arise following completion of a particular client service agenda.

Next, it will be appreciated that the system 100 of the present invention permits a user to capture, and/or record receipt of, payment from a client for an analysis, and secure a client's digital acknowledgement of the sale and the terms thereof. According to one aspect of the invention, a client report discussed below cannot be printed for a client unless and until a user has completed all predecessor tasks listed in the client service agenda, including but not limited to the analysis payment. In order for a client to definitively effect the purchase of an analysis and the resulting client report, the HSS module 135 may display a dialog asks for payment information. If a credit card is used, the number is verified to be a valid number using javascript. Other forms of payment are accepted and noted. The page also includes a java applet which allows the client to sign the device (e.g. tablet PC) using the supplied stylus. The applet saves the signature as a bitmap, assigns a file name, and returns it to the server. The server updates the client service agenda to indicate that the Analysis has been paid for Credit card information, if entered, is encrypted by a DLL before it is saved to the database. The DLL does not have the ability to decrypt the number. Once in the database, it is secure. Once transmitted to a central office, it can be decrypted and transmitted to the credit card processing service.

The system 100, and more particularly, the HSS module 135, provides a mechanism for displaying to a client the system's 100 recommendation to address the client's specific health, safety and security profile as determined by the data collected in the system 100 concerning the client. Among other data, the client report contains a combination of HSS module 135 generated responses based on predetermined solutions to known hazards, client group member profile attributes, and other assessed risks which are formulated from public health information, products available in the market, and other solutions. The report may also contain recommendations, including solutions, based upon the experience and knowledge of a user who gathers the respective client's data.

FIGS. 21 and 22 show client report GUIs 2100, 2200, according to illustrative examples and exemplary embodiments of the present invention. As a user performs an analysis inspection, notes can be added to the respective subcomponent records. These notes are then displayed on the client report. The user may also search the solution database at any point during an Analysis and relate a solution or solutions to a client as deemed necessary. Next to the quantity "drop down" dialog box on the analysis inspection page is a link to "Solutions." When clicked, the HSS module 135 pops up a dialog. On the dialog, the user can search the solution database and select one or more solutions. The search can be limited to particular types of solutions. A user can additionally browse the category tree or search by keyword, product code, UPC or manufacturer. When a solution is selected, the client report henceforth contains the new solution. A user can also identify new hazards and hazard status(es) not presented by default by the HSS module 135 for the given sublocation. At the bottom of the page is an "Add Hazard" button which allows the user to browse the hazard-hazard status database to select a hazard-hazard status combination not usually found in the current sublocation. After a new hazard is added, the HSS module 135 redraws the GUI with the additional hazard-hazard status combination added to the list. These may then be associated to a solution using the method previously described.

As solutions are selected, the data is joined together in the [Solutions] table. Among other data, a [Solutions] record contains the IDs of the [HazardStatusLinkID], the [AttributeID], the [AnswerID], and a code to indicate the type of solution. The client report provides, among other information, an aggregation of all the solutions linked via the [Solutions] table to Profile Attributes, hazard-hazard status combinations, Analysis Q&A and consultation answers. All of the data for the client report is joined together in the solution object. The client report includes, but is not limited to, the following data fields: <LocationName>, <SublocationName>, <Hazard>, <Status>, <Rationale>, <Recommendation>, <HazardQuantity>, <HazardStatistics>, <ProductQuantity>, <ProductName>, <UnitPrice>, <ExtendedPrice> and <OrderTotal>.

According to one aspect of the invention, the client report is formatted in a manner designed to maximize a client's efficiency in recognizing what a particular hazard or risk is, where it is located in the case of a physical inspection, and what the solutions thereto are that are recommended by the system 100 (and/or a user). The client report also provides a mechanism to highlight particular items which, in the opinion of the system 100 (and/or the user, based on the user's judgment and experience), are deserving of urgent attention by the client. Further, the client report provides a mechanism for displaying relevant statistics alongside the hazards identified for a particular client in order to draw additional attention to the importance of addressing such items in a timely manner. A table called [HazardStatusStats] links the hazard and hazard status to a table containing relevant statistical information. The data is stored in a text column and is displayed in the client report when a given hazard-hazard status combination is displayed. When statistics are displayed on the client report, the data may be color-coded or otherwise highlighted.

A client report is printed based upon a user i) having completed the appropriate predecessor elements of a client service agenda, ii) generating and having the client accept the terms of the analysis via the analysis quote procedure, iii) obtaining client's payment, signature, and agreement to the terms of sale via the Analysis Payment procedure, and iv) selecting the print report functionality from within the context of the client service agenda.

The system 100 records the status of each hazard-hazard status combination, consultation and Analysis Q&A answer, and analysis profile, and displays the status to a user. Inspection status is saved in each [AnalysisSublocationHazard] record. Analysis Q&A and consultation status is saved in [ConsultationAnswers]. Analysis Profile status is saved in the [AnalysisProfile] table. All records contain the client and client service agenda codes as well. Once each step is determined to have been completed (all questions and hazard-hazard status combinations either have a quantity, zero, answer, or n/a selected), the user affirms on the client service agenda that each step is either completed or N/A. At the appropriate time, the client's signature is captured by signing a Java applet using the user's device's supplied stylus. The client's signature is saved as a bitmap and the file name is stored on the respective Analysis record. The file name is a concatenation of <clientID>, <JobID>, <userID>, date and time. The directory under which the bitmap is saved is read-only to all users except the system 100 account used by the application. As a security measure, the system 100 records the activity of printing any and all client reports in its log. The client report may be printed using duplication resistant means in order to minimize the potential for unauthorized copying and distribution. A client report may also be produced online by a client via a self-service process described elsewhere herein.

Among its various sections, a client report printed by a user contains a receipt for a client's payment of the service fee for the associated Analysis, which receipt contains verbiage comprising the terms of sale, including but not limited to the 3-day "cooling off rule." According to one aspect of the invention, a client report includes: i) a form of customized solution (product and service) catalog for a client based on the data gathered and the process described, and ii) an initial representation of a client order which the client may review and utilize to determine whether client will purchase all or a portion of the solutions recommended by the system 100 via a definitive version of a client order. Alternative versions of such catalog and client report may also be generated in hard copy form, or in electronic form (on a user's) device or via the Internet). In the case of an Internet form, the catalog items collectively represent unique assemblages of solutions linked to the client's health, safety, and security profile, which perspective may be toggled "on" or "off" depending on whether a client wishes to i) view solutions for purchase based on application of the "filter" represented by the client's profile, or ii) view all potential solutions (products and services) without such "filter" or "intelligence" provided.

Client and client group member records and associated client service agenda (including the client report) created in the field are transmitted to a Central Office and stored for the purposes of order fulfillment, managerial reporting and analysis, marketing, and other objectives. The client report includes a user name and password for use by the respective client that will have certain specific functionality for a period or periods of time. Among other activities, a client may view client data, browse and order products, and perform an abbreviated self-service version of an Analysis or survey online. Through the client order and confirm order components of the system 100, a client may "complete" the process by agreeing to purchase all or some portion of the solutions recommended to the client by the system.

The system 100 provides a mechanism for ranking client's relative health, safety and security preparedness against a standard of measure and permitting the reporting of this information to a client i) via either written or verbal means delivered by a user, or ii) directly to client via the Internet in the case of a client's web-enabled self service as described herein. The system contains a table [HealthSafetyStandard]. Each record relates to a standard defined by the Company based upon third party data and/or data collected by the Company. Values from various client data tables (including but not limited to [Answers], [Attributes] and [Hazard-HazardStatusLink]) are associated to a [HealthSafetyStandard] record.

Unless delivered electronically over the Internet, the client report is typically delivered to a client in the context of a multi-section client binder which contains a variety of health, safety and security information relevant to the client. The objective of the client binder is to enhance the information contained in the client report with additional materials designed to educate the client concerning health, safety, and security issues and to increase the client's preparedness with regard thereto. The binder may include:

1. Health & Safety Analysis
Summary of Data Gathered and Resulting Solutions Recommended
2. Home (or other Facility) Health & Safety
Kitchen
Living Room and General Living Areas
Bed Room
Play Room
Bathroom
Garage Laundry Room
Porch/Patio
Grounds
Driveway
Pool/Spa
Basement
3. Medical Safety & Preparedness
Discussion
CPR and Other Training
Medical Release Form(s)
Medical Information Form(s)
4. Teaching Children About Health & Safety
Discussion
Age-based issues
Age-based education
5. Document and Data Safety
Discussion
Checklist
6. Automotive Health & Safety
7. Activity & Sports Safety
Biking, Jogging, Walking, etc.
Team Sports
Other Activities
8. Fire Emergency Preparedness
Discussion
Plan
9. Disaster Emergency Preparedness
Discussion
Plan
10. Internet and Computer Safety
11. Pet Safety
12. Personal Defense & Security
Home
Auto
Travel
13. Health & Safety Statistics
Medical
Sports
Home Accident
Fire
Disaster
Security
Crime
Other
14. Consumer Product Recalls
15. Calendar of Recommended Health & Safety Maintenance
16. Notes It will be appreciated that the system 100 provides a mechanism for a user to display for a client the contents of predetermined "kits" (collections of health, safety and/or security products in one or more containers) in categories such as medical preparedness (including, but not limited to, emergency medical products as well as general home medical care), disaster preparedness, automotive preparedness, etc. Utilizing data collected from a client, a user interacts with the system 100 to configure the ultimate contents of a kit to be sold to a client based on the customized needs of said client as determined through the data collected concerning client's lifestyle-based health, safety and security profile. Kits are collections of products. Each kit is of a defined type, such as medical kits, travel kits and emergency kits. Each kit can have multiple levels, such as "good," "better," or "best." A basic kit may have fewer or less expensive products than a higher level kit. Upon selection of a kit, a client can choose to modify the contents of the kit.

A grid is displayed with each product included in a given kit listed down the Y axis and check boxes indicating the inclusion of products in a given kit along the X axis. Products may not be removed from a kit without a substitution from a higher level kit. Additional products may be added to a kit by browsing the product inventory and selecting any product not already associated with the kit in question. The product table includes not only a retail price but a kit price. As products are added to a kit by a user or client, the total kit price in increased by the value in the respective product's "kit price" field. Kits may be sold in the context of a client service agenda or a web-based self service session by the client alone. Kit data is stored in the system 100 from a variety of tables including but not limited to [Kit], [KitLevel], [KitProductLink], [clientKit] and [clientKitProduct].

The system 100 considers each client's particular health, safety, and security profile to be unique and deserving of customized tracking. The system 100 analyzes data collected from and about each client (including but not limited to consultation responses, Analysis Q&A responses, client group member Profile Attributes, physical analysis of premises and vehicles, products offered to client for purchase, etc.) and provides a mechanism for tracking items which, in the opinion of the Company, warrant the service of providing to such client perpetual periodic notification in order to assist client in maintaining a reasonable level of preparedness regarding client's health, safety and security. Notifications include, but are not limited to, such things as: i) impending expirations of medications, batteries, car seat size/features (based on anticipated change in age/weight of child); ii) recalled items; iii) regular maintenance reminders such as smoke detector testing, chimney inspection/cleaning, important document/data backup; and iv) recommendations of products or other solutions based upon new product or service introductions relevant to client and/or the newfound relevance of such products or services to client based upon the passage of time and/or anticipated changes in the age or condition of an aspect of client's as estimated by the system.

A central office has several methods available to effect notification. Clients may be emailed individually or selected en masse by region, area code, zip code, Profile Attributes or other criteria. These client lists may then have emails broadcast to them on a given schedule, or be exported to another software program such as Access or Excel for further analysis, direct mail treatment, or the prompting of verbal communication between users and clients. The client lists are saved in the table [NotificationList]. Data fields include but are not limited to: <listname>, disttype>, <createdate>, <maildate>, <username>, <clientid>, <memberid> and <status>. A tracking and notification service can be provided to a client on an ongoing basis after the time of client's first purchase of services and/or products. An anticipated schedule of tracking and notification is available for review by the client within the context of the client service agenda and the client report.

The system 100 further supports education for clients by identifying interest from a client with regard to health, safety, and/or security-related education. By querying the client, a user determines the nature of the education desired by the client and makes arrangements for the delivery of such education for an additional fee at such time as the client desires. The system 100 can provides links to education modules in the form of Microsoft Powerpoint presentations or similar technology which may be called by the HSS module 135 and displayed to deliver education to client by a user.

According to one aspect of the invention, the system 100 can also coordinate the linking of client records with the availability of personnel who serve as a 24-hour-per-day "on call" medical information bureau designed to assist clients who have registered for the service for an additional fee with regard to medical issues they may wish to discuss via telephone with, or have handled by, trained professionals. This service envisions both general medical care as well as emergency medical care. Clients must have signed up for the service, but once they have, their unique profile is made available in the system 100 in order to structure the providing of this service.

The system 100 further provides for collecting, managing, arranging, and displaying information on health, safety, and security related products, among other purposes, in order to permit a user to demonstrate for a client the relative features, pricing, and purchasing rationale associated with products offered for sale, or products it is desirable to explicate in the context of discussions with a client, such as products with poor efficacy which clients should avoid in the opinion of the Company. Administrators or other users may insert records into the system 100 table [CompetitorPrices], which may be a list of products offered by competitors. Fields in the table include, but are not limited to: <retailername>, <productname>, <productcode>, <productprice>, <pricedate>, <shippingcost>, <catalogname> and <rationale>. Products may then be associated to competitor products via the product maintenance screen. A dialog allows for the browsing and sorting of the [CompetitorPrices] table. Clicking the product's associated check box and clicking "Add" creates the relationship in the table [CompetitorProductLink]. The client report and product browse pages both include a link to competitive products. The dialog displays an optional image of the competitive product(s), the pricing information, and the rationale behind the Company's contention that its product choice is superior. In addition to products, the system 100 can also provide a mechanism for recommending to clients various service providers whose services have been determined to be applicable to a given client's needs given the client's particular health, safety and security profile as determined by the data gathered in the system 100.

Once a client has reviewed the client report and satisfied any outstanding issues or questions, the client uses a client order procedure and electronic form (with or without the involvement of a user) to specify the final group of product(s), service(s) and other solution(s) the client wishes to purchase and in what quantity. The solution-related data contained in the client report is presented to the client in the context of a client order which is then reviewed, modified or supplemented as the client deems desirable, and approved for purchase by the respective client as described in the next section entitled "Confirm Order," at which time payment is rendered.

Upon completion of the client report via the client service agenda (or via an online self-service client survey as described elsewhere herein), the solutions produced in the client report are "frozen", and an associated client order is established. The client order consists of, but is not limited to, the tables [clientOrder] and [clientOrderSolution], where [clientOrder] comprises the header record indicating that the client report has been confirmed and that an order is either in the process of being modified or confirmed, and where [clientOrderSolution] contains the solutions and quantities specified in the client report and modified, confirmed or added during the client order review process. The fields relating to the client order include but are not limited to: <clientid>, <clientorderid>, <orderdate>, <signaturefile>, <solutionid>, <quantity>, <clientreportid> and <username>.

A user may modify the solutions contained in the client order at the direction of the client. Beyond the specific products or solutions recommended by the system 100 as solutions to a client's health, safety, and security profile, the system 100 permits the user to show to a client (and permits the client to view him- or herself online) a variety of products or solutions which may be of interest to client given client's health, safety, and security profile as identified by the system 100 through the client data gathered. The client may add items ad hoc to any list of products or solutions recommended or already ordered. The system 100 allows for browsing, searching and selection of the solution database by a variety of means, including but not limited to ID number, category, UPC, manufacturer, description and keywords. A user may select one or more products or solutions and add them to the client order. When the client order is deemed complete by the client, the user affirms that the client order is complete on the client service agenda and may then complete the confirm order process with the client.

In the case of an online self-service client session, solutions selected by the web user (client) from the client report or by browsing and searching the solutions database independently are stored in the [clientWebOrder] and [clientWebOrderSolution] tables. Each web order record contains a reference to the client, the solution and the quantity ordered. A web user (client) may search the solution database by category, keyword, UPC or any other method offered, and solutions may be added and removed and the quantities updated. A web user (client) may choose products from the solution database without benefit of a client report. solutions chosen in this manner are also stored in [clientWebOrder] and [clientWebOrderSolution]. Upon checkout, the client (web) order is considered confirmed, and payment is collected via credit card. The fields relating to the client (web) order include but are not limited to: <clientid>, <clientweborderid>, <orderdate>, <solutionid>, <quantity>, <clientreportid>, <paymentmethod>, <username>, and relevant payment and shipping information.

Once a client has conveyed to the system 100, directly or indirectly through a user, the client's election to purchase some or all of the solutions recommended by the system, the client provides final approval for the client order to be placed. The client must confirm his or her understanding of, and agreement to, all terms of sale, including but not limited to such policies as the Liability Waiver, "Cooling Off Rule," and a return policy. The client's signature is recorded along with the taking by the system 100 of a method of payment (including, but not limited to, check, credit card, debit card, hard currency). In the event the payment will be in the form of a credit card, the user (or client in the case of client's use of the online reviewing and order mechanism) records the pertinent credit card information in the system 100 for temporary storage associated with the specific client service agenda.

A client has the ability to review the hard copy client binder containing the client report and may convey to a user the client's yes/no/quantity choices with regard to recommended solutions/products for the user to record in the system 100 by annotating an electronic version of the associated client order on the user's device. Alternatively, the user and the client may review the client order together using the system 100 as a guide, with the user logging client's yes/no/quantity choices with regard to recommended solutions/products "on the fly." If a client agrees to complete a client order purchase during a user's visit, a dialog is presented. The dialog includes a text area for the client's name to be entered and a Java applet that allows the client to digitally sign the user's device (e.g. tablet PC) using the supplied stylus. The applet creates a bit map that is saved in a directory that is "read only" to all Windows® user accounts except the system 100 account used by the application. The client service agenda is updated to indicate that the client order has been confirmed and the associated bitmap file name is saved as well. If a credit card was used for the Analysis payment, the system 100 displays the last 4 digits of the card and allows the client to use the card on file to complete the client order without having to re-enter the number. If the client would like to use an alternate method of payment, the appropriate dialog is presented and payment data is collected. Alternatively, a client may call a user or a central office and confirm a client order via telephone. Additionally, a client may go to a specified site on the Internet, enter client's user name and password as provided (issued) in the client report, and review the client order online; in the event of such electronic/online review, a client shall have the ability to view detailed information about each product or solution recommended and be able to indicate whether the client will, in fact, order the item(s) in question and in what quantity. In all contexts, a client order may be modified before it is confirmed by the client.

In the event a client elects to revise client's order after it has been placed, a user may call up the client order on the system 100 and modify the client order. The client order may simply be cancelled, unless it is in the order fulfillment system, in which case the record is "locked", at which point the client's only recourse is to take receipt of the product(s) and effect a return. The client order may also be modified, in which case the original client order number is archived with a zero balance due and a revised client order is then created which contains (retains) the original client order number but adds the suffix "R-'x'". where 'x' indicates the number of the revision (e.g. if the client order is revised twice, the second revision will carry the client order number and "R-2"). The revised client order specifies all additions, deletions, and modifications from the original client order (and any subsequent revised client order). In addition to the foregoing method described in this paragraph for effecting an order revision, the client may also revise a client order by going online and modifying a previous client order in a manner similar to that described in the foregoing paragraph with regard to the original order confirmation, provided the client order has not yet reached the order fulfillment system. At such time as a client order is being revoked or modified, the system 100 forces the user to complete a short note template form to record who was involved, what happened and why; the template generates a note which is stored in the system 100 and is available in the client Information section for later reference.

Various aspects of the system 100 are managed via administration functions of the HSS module 135, including, but not limited to, the data records comprising: areas, sublocations, hazards, hazard statuses, rationales, recommendations, hazard statistics, products, product categories, consultation questions, analysis questions, question categories, users, user rights, service provider resources, resource categories, profile attributes, attribute categories, pricing, kits, and solutions. FIG. 23 shows an administration GUI 2300, according to an illustrative example and exemplary embodiment of the present invention, for selecting each of these areas.

A user utilizes the manage areas function of the system 100 to add, delete, and modify the records comprising general locations in or around a building or vehicle where a physical lifestyle-based hazard analysis will take place by a user. The data fields associated with an area include, but are not limited to, the following: <locationID>, <description>, <helptext>, <backgroundcolor>, and <sortorder>. FIGS. 24 and 25 show definition of area GUIs 2400, 2500, according to illustrative examples and exemplary embodiments of the present invention.

A user utilizes the manage sublocations section of the system 100 to add, delete, and modify the records comprising specific locations in or around a building or vehicle (and within a general area as defined hereinabove), where a physical lifestyle-based hazard analysis will take place by a user. The data fields associated with a sublocation include, but are not limited to, the following: <sublocationID>, <description>, <title>, <helptext>, <indoor>, and <outdoor>. Once a sublocation has been created, a user uses the system 100 to associate the sublocation record with one or more areas wherein such sublocation might logically be expected to be found (note: a user has the ability to associate an unexpected sublocation with any Area on an ad hoc basis if the physical layout of a client's inspection area should require it—e.g. an outdoor kitchen). As described earlier, areas ([Locations] and [Sublocations]) are selected independently and therefore can exist in any number of combinations. FIGS. 26 and 27 show definition of subarea GUIs 2600, 2700, according to illustrative examples and exemplary embodiments of the present invention.

A user utilizes the manage hazards section of the system 100 to add, delete, and modify the records comprising specific hazards which might reasonably be expected to be found in or around a building (and within an area and sublocation as defined hereinabove) or vehicle during the course of a physical lifestyle-based hazard analysis by a user. The data fields associated with a hazard include, but are not limited to, the following: <hazardID>, <description>, <title> and <recommendation>. Once a hazard has been created, a user uses the system 100 to associate the hazard record with one or more sublocations wherein such a hazard might logically be expected to be found. hazards inherit relationships with areas through the area and sublocation association process described hereinabove. The system displays a dialog prompting the user to select a location, sublocations. Hazards not already associated to the combination of LocationID and SublocationID are listed. The results can be sorted or searched and multiple selections may be made. On the sublocation page, a user is presented with a listing of available hazard—hazard status combinations. Each combination has an associated check box which, when checked, indicates that it should be linked to the [Sublocation]. When the "add" button is checked, the association is made. Likewise currently selected hazard—hazard status combinations can be removed from the link by clicking the associated check box and clicking the "Remove" button. Selections are saved in the [HazardSublocationLink] table. When selected the user may choose to indicate that this combination of hazard-hazard status and sublocation requires urgent attention. If the urgent flag is set, the analysis inspection and client report will both indicate the urgency. During an analysis inspection, a user may choose to add hazard-hazard status combinations to a sublocation on an ad hoc or as needed basis. These are added to the client report. The system also allows for hazards to be added and associated at this time. FIGS. 28-30 shows a hazard definition and association GUIs 2800, 2900, 3000, according to illustrative examples and exemplary embodiments of the present invention.

A user utilizes the manage hazard statuses section of the system 100 to add, delete, and modify the records comprising specific statuses which might reasonably be expected to apply to hazards found in or around a building (and within an area and sublocation as defined hereinabove) or vehicle during the course of a physical lifestyle-based hazard analysis by a user. The data fields associated with a hazard status include, but are not limited to, the following: <HazardStatusID>, <Description>, <Title>, <HelpText>, <Rationale> and <Recommendation>. Key elements of the hazard status record are the rationale and the recommendation. The rationale details the specific risk(s) that each listed combination of a hazard and hazard status represent to a client, based on public safety statistics and other sources. The recommendation provides a description of the specific solution(s) recommended to eliminate or mitigate a particular hazard and hazard status combination, based on public safety statistics and other sources. Once a hazard status has been created, a user uses the system 100 to associate the hazard status record with one or more hazards with regard to which such a hazard status might logically be expected to be encountered. The results may be sorted and searched, and multiple selections can be made. New hazard statuses can also be added and associated. Hazards Statuses inherit relationships with Areas and sublocations through the Area, sublocation and hazard association process described hereinabove. FIGS. 31-32 show a hazard status and detailed hazard association GUIs 3100, 3200, according to illustrative examples and exemplary embodiments of the present invention.

A user utilizes the manage products section of the system 100 to add, delete, and modify the records comprising specific products which the system 100 will offer as solutions to correct or mitigate the effect(s) of: i) the hazards found in or around a building (and within an Area and sublocation as defined hereinabove) or vehicle during the course of a physical lifestyle-based hazard analysis by a user, and ii) other risks which may pertain to the client based upon client's particular lifestyle-based health, safety and security profile or concerns. The data fields associated with a product include, but are not limited to, the following: <ProductID>, <UPC>, <ProductTitle>, <ProductDescription>, <Height>, <Weight>, <Thumbnailpath>, <ZoomPath>, <MedTracerProduct>, <ReplacesProductID>, <EstimatedInstallTime>, <InstallationInstructions>, <BenefitsUsage>.

Once a product has been entered into the system, a user uses the system 100 to associate the product record with i) one or more combinations of hazards and hazard statuses with regard to which such a product would serve to eliminate or mitigate the associated Risk(s), and ii) other data records whereby the resulting association serves to offer a solution to a client's lifestyle-based health, safety and security profile or concerns. FIGS. 33-34 show product and sublocation hazard status GUIs 3300, 3400, respectively, according to illustrative examples and exemplary embodiments of the present invention. The system 100 provides a mechanism to link products to pricing data in order to generate a client report and client order. The products recommended by the system 100 appear in the client report associated with each appropriate hazard, risk, or concern identified by the user during his or her analysis. From the product GUI a dialog is shown which lists predefined sublocations, hazards and hazard statuses. The list may be sorted by all columns and is searchable. Multiple entries can be made, each one indicating a link to a hazard status. The Defined sublocations page shows all joins between sublocations, hazards and hazard statuses. The user selects a predefined combination and is prompted with the currently associated products or solutions. From this page, products or solutions may be removed from the list or a dialog can be presented which lists products or solutions not already associated to the sublocation-hazard-hazardstatus set.

A user utilizes the product category GUI 3500 to add, delete, and modify the records comprising specific product categories with which all of the products and solutions described hereinabove become associated in order to accomplish structure and efficiency in the organization and display of said products for the benefit of users and clients. The data fields associated with a product category include, but are not limited to, the following: <CategoryName>, <CategoryID>, <CategoryDesc>, <ParentCategoryId>, <ChildCategoryID>. Once a product category has been entered into the system, a user uses the system 100 to associate the product category record with one or more products. Among other purposes, the product categories assist in facilitating searches for products of a particular type as well as for organizing and displaying information about similar products for purposes of product comparisons, sales assistance, training, and client order creation. From the product maintenance screen, a dialog allows the user to navigate the category structure. The structure is completely open-ended, with every category a possible parent and child. Once the tree has been navigated and the proper category or categories found, a user selects the category(-ies). The record is inserted into the [ProductCategoryLink] table. The product is then available wherever that category exists in the category tree.

A user utilizes a manage injury statistics function of the system 100 to add, delete, and modify the records comprising specific public health and safety statistics which the system 100 uses, among other purposes, to report to a client additional information relevant to client-specific risks, including but not limited to the particular hazards found in or around a building (and within an Area and sublocation as defined hereinabove) or vehicle during the course of a physical lifestyle-based hazard analysis by a user. The data fields associated with an Injury Statistic include, but are not limited to, the following: <InjuryStatisticID>, <HazardID>, <HazardStatusID>, <InjuryStatistic>, <DataSource>, <ImageName>, <ReferenceURL>, <Population>, <NumberOfinjuries>, <CrudeRate> and <AgeAdjustedRate>. Once an Injury Statistic has been entered into the system, a user uses the system 100 to associate the Injury Statistic record with one or more combinations of hazards and hazard statuses with regard to which such an Injury Statistic would be applicable in order to highlight the associated risk(s). The Injury Statistics may appear in the client report associated with each appropriate line item hazard identified by the user during his or her analysis. Each hazard-hazard status combination can be associated to multiple Injury Statistics records.

A user utilizes the manage questions function of the system 100, and more particularly, questionnaire creation GUIs 3600, 3700 shown in FIGS. 36 and 37, to add, delete, and modify the records comprising specific questions which a user will ask of a client during the course of a consultation. The data fields associated with a Question include, but are not limited to, the following: <QuestionID>, <QuestionText>, <Order>, <EssayQuestion> (yes/no), <CategoryId>, <QuestionTypeID> (Analysis Q&A or consultation). Once a Question has been entered into the system, a user uses the system 100 to associate the Question record with i) one or more Question Categories (see below), and ii) the context of a consultation. As mentioned above, a consultation is a process whereby a user interacts with a client to assist the client in determining whether the client desires to purchase products or other solutions, including but not limited to an analysis. Among other purposes, the consultation questions assist the user in gathering pertinent information from the client to identify and provide solutions (including, but not limited to, products, services, recommendations, training) pertaining to client's health, safety and security-related profile. Questions may be moved back and forth between use in consultation and analysis depending on where the questions may more logically fall with regard to the context, structure and timing of a user's communication with a client. The questionnaire creation GUIs include two radio buttons which indicate which type the question is. If the <QuestionTypeID> is "1", it is a consultation question. If the <QuestionTypeID> is "2", it is an Analysis Q & A question.

A user utilizes the manage question category GUI 3800 of FIG. 38 to add, delete, and modify the records comprising specific health, safety, and security-related categories designed to appropriately organize communication flow between a user and a client during the course of a consultation or an analysis Q&A. The data fields associated with a Question Category include, but are not limited to, the following: <CategoryID>, <CategoryText>, <Sort>. Once a question category has been entered into the system, a user uses the system 100 to associate the question category record with one or more questions. The question maintenance page includes a selection of available question categories. A user makes the selection and saves the record.

FIG. 39 shows a manage profile attributes GUI 3900, according to an illustrative example and exemplary embodiment of the present invention. A user utilizes the GUI 3900 to add, delete, and modify the records comprising specific lifestyle-based health, safety, and security-related issues and topics about which a user will query a client during the course of an analysis profile. The data fields associated with profile attributes include, but are not limited to, the following: <AttributeID>, <AttributeName>, <Details>, <ProfileListID>, <ProfileListName>, <ValueID>, <Value>, <Describe> (yes/no indicating that an explanation is required during the analysis profile). Once a profile attribute has been entered into the system 100, a user uses the system 100 to associate the profile attribute record with one or more other records in the system 100 (including but not limited to solutions, resources, products, kits, Recommendations, and Statistics) to enable relationships between profile attribute data and solutions (including, but not limited to, products, services, recommendations, and training) which will be recommended to the client by the system 100 pertaining to client's lifestyle-based health, safety and security-related profile. As mentioned above, an analysis profile is a process whereby a consultant interacts with a client to gather pertinent information from the client in order to identify and provide solutions (including, but not limited to, products, services, recommendations, and training) pertaining to client's health, safety and security-related profile. The system 100 displays a grid with each client group member across the top (X axis) and Yes/No questions along the Y axis. Each intersection of a client group member and an Attribute (or question) is represented by a checkbox. By clicking in the checkbox, a user indicates that the answer is "yes". Values are stored in [MemberAttribute]. Similarly, each question with more than one answer (Profile List) is displayed along the Y axis. Each column associated with a client group member contains a selection of values from [ProfileListValues]. Selected values are stored in [MemberProfileList].

FIG. 40 shows a user rights hierarchy GUI 4000, according to an illustrative example and exemplary embodiment of the present invention. A user with Administrative (managerial) authority utilizes the user rights hierarchy GUI 4000 to add, delete, and modify the records comprising the specific users who have the right to access and use the system. Each user is granted certain rights within the system 100 based upon a predefined hierarchy of permissions, which rights may be amended or cancelled as deemed appropriate by a user (Administrator) having sufficient authority within the system 100. The data fields associated with a user record include, but are not limited to, the following: <userName>, <FirstName>, <LastName>, <EmailAddress>, <PhoneNumber>, <FaxNumber>, <MobileNumber>, <Password> and <Status>.

Once a user record has been entered into the system, a user (Administrator) uses the system 100 to associate the user record with certain rights based upon the user's role within the structure of the Company. Roles are defined in the [Role] table. They are used to manage the behavior of the system 100 as it pertains to various classes of user, including but not limited to: Management, Lead consultant, Associate consultant, Warehouse Manager, Controller, and client. Among other data, the table [userRole] contains the <ComputerID>, <userName> and <RoleID>. By searching the table for the combination, a given user can be limited to different roles depending on the ID of the computer being used or the specific username and password of the user. If the computer ID is left Null, the respective role is valid on all computers.

It will be appreciated that the system 100 permits an Administrator to define a user rights hierarchy which specifies the screens, functions, and activities a given user or group of users shall have access to and use of within the system. The user rights hierarchy defines levels of authority, tied in most cases to the respective relationship between a given user and the Company (and, if applicable, job title or managerial level). User rights are managed via the user Roles described in Section 5(1) above. The following list, though not exhaustive, describes a variety of the authorization levels with which a given user may have his or her user Record associated in order to provide access to and use of system 100 functionality: Executive, HazardMaintenance, StatisticMaintenance, QuestionMaintenance, ProductMaintenance, AttributeMaintenance, VendorMaintenance, Purchasing, WarehouseGeneral, WarehouseAdmin, LeadsMaintenance, userMaintenance and Scheduling.

The system 100 also provides a mechanism for maintaining information regarding persons or entities that a user or the system 100 may utilize to recommend to a client in order to assist client with regard to completing recommended solutions to the client's health, safety and security needs as identified through a client service agenda. Such persons or entities include, but are not limited to, installers, craftsmen, lawyers, financial advisors, contractors, trainers, Internet web-sites (URLs), and physicians. Further, the system 100 provides mechanisms for assessing the qualifications of said persons or entities with regard to their suitability for providing services to a client at the recommendation of a user (or the system). The system 100 maintains the list of Resources in the [ProviderResource] table. Each [ProviderResource] record contains standard contact information as well as links to [HazardStatuses], [ProfileAttributes] and answers to Analysis Q & A and the consultation questions via the [Solutions] table. Each [Solutions] record contains the ID of the applicable [Hazard-HazardStatusLink], attribute, answer, a code to indicate the type of solution. Such data is provided in the client report with the other solutions recommended or selected by the system. Provider resources are also linked to zip codes which they service. The system 100 aggregates the data from the client service agenda and recommends provider resources in the client's area in either a client report or in the context of a self-service client web session.

The system 100 provides a mechanism whereby a user may add, delete, and modify records comprising specific service provider resource categories designed to appropriately organize communication flow between a user and a client in discussing which resources might be brought to bear to eliminate or mitigate a client's particular health, safety and/or security related issues. The data fields associated with a service provider resource Category include, but are not limited to, the following: <ProviderID>, <ProviderName>, <Address>, <PhoneNumber>, <FaxNumber>, <CellNumber>, <EmailAddress>, <WebSite>, <ReferralDiscount> and <AssociatedZipCodes>. Once a service provider resource category has been entered into the system 100, a user uses the system 100 to associate the service provider resource category record with one or more resources.

A user may utilize a manage kit contents function of the system 100 to add, delete, and modify the records comprising specific kits (pre-defined collections of products) which the system 100 will offer as solutions to correct or mitigate the effect(s) of: i) the hazards found in or around a building (and within an Area and sublocation as defined hereinabove) or vehicle during the course of a physical lifestyle-based hazard analysis by a user, and ii) other risks which may pertain to the client based upon client's particular lifestyle-based health, safety and security profile or concerns. The data fields associated with kit contents include, but are not limited to, the following: <KitName>, <KitDescription>, <KitRationale>, <KitID>. Once a kit Contents "group" has been entered into the system 100, a user uses the system 100 to associate the kit contents record with i) one or more combinations of hazards and hazard statuses with regard to which such a kit would serve to eliminate or mitigate the associated risk(s), and ii) other data records whereby the resulting association serves to offer a solution to a client's lifestyle-based health, safety and security profile or concerns. The system 100 provides a mechanism to link kits to pricing data in order to generate its component of a client order. The kits recommended by the system 100 appear in the client report associated with the appropriate hazard, risk, or concern identified by the user during his or her Analysis.

After choosing or adding a kit, the user is presented a grid. Each column of the grid represents a pre-defined level (e.g. "good", "better", "best"). Selected products exist on the Y axis and 2 checkboxes exist in each cell representing the intersection of selected products and kit levels. The first checkbox represents "include", meaning that, when checked, the respective product is included in that level of the kit. The second checkbox represents "required", meaning that, when checked, that particular product may not be removed or a substitute chosen during the client order review and confirmation process. A button at the bottom labeled "Add Product" navigates to pages which allow the product database to be searched and products chosen. At the top of the "browse" page for additional products, check boxes indicate the levels and required status to be used when the product is added. Once a product or products are chosen, the kit maintenance screen is displayed including the new product or products.

The system 100 provides a mechanism for maintaining pricing information regarding products, kits, resources, training, services and other solutions that a user may associate with other records in the system 100 in order to generate a client order. The table [ProductPrice] contains the pricing information. It contains, but is not limited to, the <ProductID>, <PriceLevel> and the date range for which the price is valid. This maintains a product price history as well as different prices for promotional and other purposes.

The system 100 provides a mechanism for collecting, organizing, and displaying product (solution) description, feature, and price information concerning items sold by the Company as well as other products. A portion of this functionality is related specifically to the maintenance of comparative pricing information so that a user may display for a client information concerning products in order to demonstrate the difference between the price to be charged by the Company as compared with the price charged by other sellers of the same or a similar product. The data fields associated with the Comparative product and Pricing Data include but are not limited to: <CompetitorPriceID>, <ProductID>, <Retail>, <Shipping>, <Catalog>, <PriceDate>, <RetailerName> and <Notes>. A user selects Comparative product and Pricing Data from the Administration menu and utilizes the associated interface to enter information about each product. For each respective product, the system 100 stores multiple records concerning alternative retailer offerings. Subsequently, in the context of a client service agenda discussion with a client (including but not limited to an Order Confirmation), the user may click on any product name hotlink to display for a client additional information concerning said product as well as comparative product information and price data. The purpose of this functionality is to demonstrate for a client i) the relative cost efficiency of purchasing a given product or solution from the Company compared with other potential sources of said product or solution, and ii) the relative efficacy of said product solution as compared with other potential solutions for mitigating the same perceived risk. Each [CompetitorPrice] record contains the <ProductID> of the item it competes with. The client report contains a link for each product (or solution) which has Competitor Prices entered.

The system 100 provides a mechanism for hierarchical control of information flow and activity based on different user's authorization levels, including, but not limited to, interaction between personnel in the field and one or more Central Offices. Once a given user has been established in the system, and once said user's authorization level has been established, the user may utilize any of the software functionality to which he or she has been given the right of access and use. Certain flows of information and activity are based upon user involvement with the system 100 (e.g. a routine data synchronization between a user's device and a Central Office server), while others are automatic in nature (e.g. a product expiration notification to a client prompted by the system's monitoring of the passage of time against a client's data profile). The Headquarters Central Office houses the corporate database and code. Each regional or local office connects to the Central Office via dialup or a dedicated connection. Upon login, the system 100 automatically limits views to those appropriate for the user. Tool-based permissions in combination with regional or local identifiers give each office/user its own unique view of the data. The clients, leads, users and management data presented are all filtered by the regional or local identifier, or in the case of a Central Office, a filter can be applied or removed to see any combination of regional areas. The following list, though not exhaustive, describes a variety of the types of data exchange between users that comprise the Company's operational command and control mechanisms:

New Leads
Lead Status
Appointments
consultants
clients
Analysis Data
Inspection Data
client orders
consultant client Lists
System Data (hazards, hazard statuses, Questions, Answers, solutions, etc.)

The system 100 provides a mechanism for managing the product inventory associated with the Company's offering of items to solve a client's lifestyle-based health, safety and security issues. All products are logged into the system 100 and tracked with regard to a variety of criteria. The data fields associated with Inventory Management include but are not limited to: <VendorID>, <VendorName>, <Height>, <Width>, <Weight>, <ProductName>, <UPC>, <ItemNumber>, <LeadTime>, <QuantityOnHand>, <QuantityOnOrder>, <PendingSales>, <PendingPurchaseOrders>, <Minimum> and <ReorderQuantity>. Price is contained in the [ProductPrice] table which contains, among other data, <PriceID>, <ProductID>, <Quantity>, <Cost> and <Retail>. This allows for <Cost> and <Retail> sales to be calculated using either LIFO or FIFO. Among other tasks, the Inventory Management mechanism tracks incoming products, logs key data elements (e.g. respective product expiration dates), manages the product fulfillment process, and initiates the purchase order process for re-orders as well as vendor direct drop shipments. Sales of products to clients trigger processes within the Inventory Management mechanism to pick and deduct items from inventory, set up product expiration notice timeframes, schedule deliveries, and provide notification that new inventory must be acquired to maintain an adequate buffer. Pending Sales are sales that have been received from consultants but not fulfilled. This allows the Sale to be deducted from Inventory but then added back if the sale is canceled. The system 100 allows for forecasting in various increments. Sales and Purchases are aggregated nightly into a record containing the <ProductID>, <Month> and <Quantity>. Sales can then be charted over any period. Additionally a process runs each night to update the Monthly On-Hand Quantity. Alerts are automatically generated if a trend up or down is detected or if the system 100 predicts an impending shortage or overage. The system 100 records the vendor from which a given item was purchased as well as any relevant "serial number", "expiration" or "batch number" to enable tracking medications or other items from a "recall" or other perspective pertaining to post-sale client notification(s).

The system 100 provides a mechanism to analyze all relevant client data in order to determine additional opportunities for associating anticipated client needs with solutions to recommend over time to a client based upon anticipated changes in client's profile (such as changes in children's ages, medical history, etc.) or other factors (such as new product introductions, etc.). A user may associate products, kits, services or other solutions with hypothetical client profiles and then utilize the system 100 to identify clients whose profiles match the hypothetical examples in order to initiate opportunities to market such additional products or services to clients through or assisted by the system. Profiles are built with a variety of data, including but not limited to hazard-hazard status combinations, Profile Attributes, answers to consultation and Analysis Q&A questions, age and sex information. Solutions are associated with these profiles. The system then returns a list of clients that match the relevant characteristics. Lists are editable. The data is exportable into other programs such as Excel or Access, or HTML Emails can be created and scheduled to be broadcast to the Primary or relevant client group member(s).

Many modifications and other embodiments of the inventions set forth herein will come to mind to one skilled in the art to which these inventions pertain having the benefit of the teachings presented in the foregoing descriptions and the associated drawings. Thus, it will be appreciated by those of ordinary skill in the art that the present invention may be embodied in many forms and should not be limited to the embodiments described above. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer program product for use with a data processing system for gathering and conducting lifestyle-based analyses, said computer program product comprising a computer usable medium having computer-readable code means embodied in said medium, said computer-readable code means comprising:
   computer readable program code means for receiving safety information representative of one or more potential safety hazards existing at a client location input into said computer program product;
   computer readable program code means for evaluating said safety information to identify the potential safety hazards existing at the client location, said safety information being generated as a result of an analysis of said client location; and
   computer readable program code means for providing an electronic recommendation, based upon the identified potential safety hazards, of one or more products or services to mitigate or eliminate the identified potential safety hazards, said recommendation being generated through the use of stored data that links the safety hazards to the one or more products or services for mitigating or eliminating the identified potential safety hazards.

2. The computer program product of claim 1, wherein said computer usable medium further comprises computer-readable code means for receiving security information related to potential security hazards existing at the client location input into said computer program product, said security information being generated as a result of an analysis of said client location.

3. The computer program product of claim 2, wherein said computer usable medium further comprises computer-readable code means for evaluating said security information to identify the potential security hazards existing at the client location.

4. The computer program product of claim 3, wherein said computer usable medium further comprises computer-readable code means for recommending, based upon said security hazards, one or more products or services to mitigate or eliminate said security hazards existing at the client location.

5. The computer program product of claim 1, wherein said computer usable medium further comprises computer-readable code means for receiving health information related to potential health hazards at the client location input into said computer program product, said health information being generated as a result of analysis of said client location.

6. The computer program product of claim 5, wherein said computer usable medium further comprises computer-readable code means for evaluating said health information to identify the potential health hazards at the client location.

7. The computer program product of claim 6, wherein said computer usable medium further comprises computer-readable code means for recommending, based upon said health hazards, one or more products or services to mitigate or eliminate said potential health hazards existing at the client location.

8. The computer program product of claim 1, wherein said computer usable medium is accessible via a Wide Area Network (WAN).

9. The computer program product of claim 1, wherein said computer program product comprises a software program.

10. The computer program product of claim 1, wherein said computer program product resides in a device selected from devices consisting of a laptop computer, a server, a personal computer, a personal digital assistant, a hand held computer, and a portable computer.

11. A method for conducting lifestyle-based analyses, comprising:
- collecting safety information related to potential safety hazards existing at a client location, the safety information being generated as a result of an analysis of the client location;
- storing product and service information, wherein said product and service information relates to one or more products or services for mitigating said potential safety hazards;
- storing data linking the potential safety hazards to the products and services for mitigating the potential safety hazards; and
- using the stored data to transform the stored safety information and the product and service information into an electronic recommendation of one or more products or services for mitigating or eliminating said potential safety hazards existing at the client location.

12. The method of claim 11, further comprising the steps of collecting security information related to potential security hazards existing at the client location, the security information being generated as a result of an analysis of the client location.

13. The method of claim 12, wherein the step of storing further includes the step of storing product and service information relating to one or more products or services for mitigating said potential security hazards, and wherein the transforming operation further comprises transforming said security information into an electronic recommendation of one or more products or services for mitigating said potential security hazards.

14. The method of claim 11, further comprising the steps of collecting health information related to potential health hazards existing at the client location, the health information being generated as a result of an analysis of the client location.

15. The method of claim 14, wherein the step of storing further includes the step of storing product and service information relating to one or more products or services for mitigating said potential health hazards, and wherein the transforming operation further comprises transforming said health information into an electronic recommendation of one or more products or services for mitigating said potential health hazards existing at the client location.

16. The method of claim 15, further comprising the step of monitoring a client profile and using said profile to automatically identify said one or more products or services for mitigating said potential health hazards.

17. The method of claim 11, further comprising the step of monitoring a client profile and using said profile to automatically identify said one or more products or services for mitigating said potential safety hazards.

18. The method of claim 13, further comprising the step of monitoring a client profile and using said profile to automatically identify said one or more products or services for mitigating said potential security hazards.

19. The method of claim 11, further comprising generating a score comparing the preparedness of a client in relation to a standard determined using at least one reference selected from references consisting of public accident statistics, disaster statistics, injury statistics, health statistics and/or other statistics or information generated by a company.

20. A system for gathering and conducting lifestyle-based analyses, comprising:
- at least one input device, said at least one input device operable to receive data related to health, safety and/or security hazards existing at a client location, the data related to health, safety and/or security hazards existing at a client location being generated as a result of an analysis of the client location;
- at least one storage medium, in communication with said at least one input device, said at least one storage medium configurable to store said data related to client specific health, safety and/or security hazards and to store data linking the health, safety, and/or security hazards to product and/or service recommendations to mitigate or eliminate the health, safety, and/or security hazards; and
- at least one program, said at least one program operable to use the stored data linking the hazards to product and/or service recommendations to transform said data related to specific health, safety and/or security hazards existing at the client location into one or more electronic product and/or service recommendations to mitigate or eliminate said client specific health, safety and/or security hazards existing at the client location.

21. The system of claim 20, wherein said at least one input device is in remote communication with said at least one storage medium.

22. The system of claim 21, wherein said at least one input device and said at least one storage medium are in communication via the Internet.

23. The system of claim 20, wherein said at least one program is in remote communication with said at least one input device.

24. The system of claim 20, further comprising an output device, said output device operable to display said product and/or service recommendations to mitigate or eliminate said health, safety and/or security hazards.

25. The system of claim 20, wherein said at least one program is operable to generate electronic quotes and/or estimates of services and/or products corresponding to the product and/or service recommendations to mitigate or eliminate said health, safety and/or security hazards.

26. The system of claim 25, wherein said quote and/or estimates are displayed via an output device.

27. The system of claim 25, wherein said at least one program is operable to track the expiration dates of said products corresponding to the product recommendations to mitigate or eliminate said health, safety and/or security hazards.

28. The system of claim 27, wherein said at least one program is operable to identify when said expiration dates have expired.

29. The system of claim 20, wherein said at least one program is further operable to compare said product and/or service recommendations.

30. A computer-implemented method for gathering lifestyle-based health, safety and security risks and conducting associated analyses, comprising:
- collecting, at a client location or over the Internet, health, safety, and security information related to potential health risks, safety hazards, and security concerns existing at a client location;
- gathering product, service, and behavioral modification, wherein said product, service, and suggested behavioral modification information relates to one or more products or services for mitigating or eliminating said potential health risks, safety hazards, or security concerns;

storing data pre-linking the potential health risks, safety hazards, and security concerns to the products or services for mitigating or eliminating said potential health risks, safety hazards, or security concerns;

identifying, using said stored data, said one or more products, services, and suggested behavioral modifications for mitigating or eliminating said potential health risks, safety hazards or security concerns; and assembling an electronic order for purchasing said one or more products or services based upon said potential health risks, safety hazards or security concerns.

* * * * *

UNITED STATES PATENT AND TRADEMARK OFFICE
CERTIFICATE OF CORRECTION

| | | |
|---|---|---|
| PATENT NO. | : 7,606,783 B1 | Page 1 of 1 |
| APPLICATION NO. | : 11/382702 | |
| DATED | : May 10, 2006 | |
| INVENTOR(S) | : Robert M. Carter | |

It is certified that error appears in the above-identified patent and that said Letters Patent is hereby corrected as shown below:

Beginning at Column 40, line 55 through Column 42, line 5 should read as follows:

30. A computer-implemented method for gathering lifestyle-based health, safety and security risks and conducting associated analyses, comprising:

collecting, at a client location or over the Internet, health, safety, and security information related to potential health risks, safety hazards, and security concerns existing at a client location;

gathering product, service, and behavioral modification <u>information</u>, wherein said product, service, and suggested behavioral modification information relates to one or more products or services for mitigating or eliminating said potential health risks, safety hazards, or security concerns;

storing data pre-linking the potential health risks, safety hazards, and security concerns to the products or services for mitigating or eliminating said potential health risks, safety hazards, or security concerns;

identifying, using said stored data, said one or more products, services, and suggested behavioral modifications for mitigating or eliminating said potential health risks, safety hazards or security concerns; and assembling an electronic order for purchasing said one or more products or services based upon said potential health risks, safety hazards or security concerns.

Signed and Sealed this

Tenth Day of August, 2010

David J. Kappos
*Director of the United States Patent and Trademark Office*